(12) United States Patent
Braun et al.

(10) Patent No.: US 9,512,113 B2
(45) Date of Patent: Dec. 6, 2016

(54) N-(TETRAZOL-5-YL)- AND N-(TRIAZOL-5-YL)ARYLCARBOXYLIC THIOAMIDES AND USE THEREOF AS HERBICIDES

(71) Applicant: BAYER CROPSCIENCE AG, Monheim (DE)

(72) Inventors: Ralf Braun, Ramberg (DE); Simon Doerner-Rieping, Neu-Anspach (DE); Hartmut Ahrens, Egelsbach (DE); Arnim Koehn, Klein-Winternheim (DE); Christian Waldraff, Bad Vilbel (DE); Hansjoerg Dietrich, Liederbach am Taunus (DE); Dirk Schmutzler, Hattersheim (DE); Elmar Gatzweiler, Bad Nauheim (DE); Christopher Hugh Rosinger, Hofheim (DE)

(73) Assignee: Bayer Cropscience AG, Monheim (DE)

( * ) Notice: Subject to any disclaimer, the term of this patent is extended or adjusted under 35 U.S.C. 154(b) by 0 days.

(21) Appl. No.: 14/401,177

(22) PCT Filed: May 22, 2013

(86) PCT No.: PCT/EP2013/060464
§ 371 (c)(1),
(2) Date: Nov. 14, 2014

(87) PCT Pub. No.: WO2013/174843
PCT Pub. Date: Nov. 28, 2013

(65) Prior Publication Data
US 2015/0175588 A1 Jun. 25, 2015

(30) Foreign Application Priority Data
May 24, 2012 (EP) .................... 12169234

(51) Int. Cl.
*C07D 257/06* (2006.01)
*C07D 413/12* (2006.01)
*C07D 403/12* (2006.01)
*C07D 401/12* (2006.01)
*C07D 249/14* (2006.01)
*A01N 41/10* (2006.01)
*A01N 43/42* (2006.01)
*A01N 43/713* (2006.01)
*A01N 43/80* (2006.01)

(52) U.S. Cl.
CPC ............ *C07D 413/12* (2013.01); *A01N 41/10* (2013.01); *A01N 43/42* (2013.01); *A01N 43/713* (2013.01); *A01N 43/80* (2013.01); *C07D 249/14* (2013.01); *C07D 257/06* (2013.01); *C07D 401/12* (2013.01); *C07D 403/12* (2013.01)

(58) Field of Classification Search
CPC ..................................... C07D 257/06
USPC ......................... 548/251; 504/261
See application file for complete search history.

(56) References Cited

U.S. PATENT DOCUMENTS

| 8,481,749 | B2 | 7/2013 | Braun et al. |
| 9,035,064 | B2 | 5/2015 | Koehn et al. |
| 9,101,141 | B2 | 8/2015 | Koehn et al. |
| 2014/0080705 | A1 | 3/2014 | Koehn et al. |
| 2014/0323301 | A1 | 10/2014 | Braun et al. |

FOREIGN PATENT DOCUMENTS

| EP | 0049071 A1 | 4/1982 |
| EP | 11158253 | 3/2011 |
| EP | 11159115 | 3/2011 |
| WO | 2012028579 A1 | 3/2012 |
| WO | 2012/123416 A1 | 9/2012 |
| WO | 2012/126932 A1 | 9/2012 |
| WO | 2012123416 A1 | 9/2012 |
| WO | 2012126932 A1 | 9/2012 |
| WO | 2012028579 A1 | 3/2013 |
| WO | 2013064458 A1 | 5/2013 |

OTHER PUBLICATIONS

Dorwald, Side Reactions in Organic Synthesis, 2005, Wiley: VCH Weinheim Preface, pp. 1-15 & Chapter 8, pp. 279-308.*
International Search Report from corresponding PCT/EP2013/060464, mailed Jun. 24, 2013.

* cited by examiner

*Primary Examiner* — Patricia L Morris
(74) *Attorney, Agent, or Firm* — McBee Moore Woodward Vanik IP LLC

(57) ABSTRACT

N-(Tetrazol-5-yl)- and N-(triazol-5-yl)arylcarboxylic acid thioamides of the general formula (I) are described as herbicides.

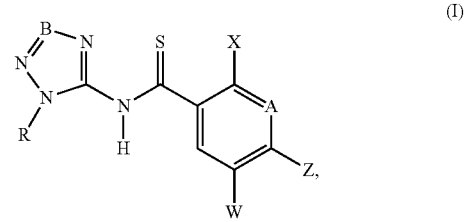

In this formula (I), R, W, X and Z represent radicals such as hydrogen, organic radicals such as alkyl, and other radicals such as halogen. A and B each represent carbon or nitrogen.

12 Claims, No Drawings

N-(TETRAZOL-5-YL)- AND N-(TRIAZOL-5-YL)ARYLCARBOXYLIC THIOAMIDES AND USE THEREOF AS HERBICIDES

CROSS REFERENCE TO RELATED APPLICATIONS

This application is a §371 National Stage Application of PCT/EP2013/060464, filed May 22, 2013, which claims priority to EP 12169234.7, filed May 24, 2012.

BACKGROUND

1. Field of the Invention

The invention relates to the technical field of herbicides, especially that of herbicides for the selective control of broad-leaved weeds and weed grasses in crops of useful plants.

2. Description of Related Art

WO 2012/028579 A1 discloses N-(tetrazol-5-yl)- and N-(triazol-5-yl)nicotinamides as herbicides. However, these active compounds are not always sufficiently active against harmful plants and/or some of them are not sufficiently compatible with some important crop plants such as cereal species, corn or rice.

Accordingly, it is an object of the present invention to provide further herbicidally active compounds. This object is achieved by the N-(tetrazol-5-yl)- and N-(triazol-5-yl) arylcarboxylic acid thioamides according to the invention described below which, owing to the thioamide structure, differ substantially from the compounds known from the prior art.

SUMMARY

The present invention thus provides N-(tetrazol-5-yl)- and N-(triazol-5-yl)arylcarboxylic acid thioamides of the formula (I) or salts thereof

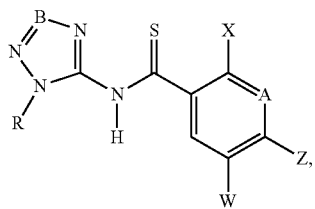

(I)

in which

A represents N or CY,

B represents N or CH,

X represents nitro, halogen, cyano, formyl, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $COOR^1$, $OCOOR^1$, $NR^1COOR^1$, $C(O)N(R^1)_2$, $NR^1C(O)N(R^1)_2$, $OC(O)N(R^1)_2$, $C(O)NR^1OR^1$, $OR^1$, $OCOR^1$, $OSO_2R^2$, $S(O)_nR^2$, $SO_2OR^1$, $SO_2N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $NR_1R_2$, $P(O)(OR^5)_2$, $CH_2P(O)(OR^5)_2$, $(C_1-C_6)$-alkylheteroaryl or $(C_1-C_6)$-alkyl-heterocyclyl, where the two last-mentioned radicals are each substituted by s radicals from the group consisting of halogen, $(C_1-C_6)$-alkyl, halo-$(C_1-C_6)$-alkyl, $S(O)_n$—$(C_1-C_6)$-alkyl, $(C_1-C_6)$-alkoxy and halo-$(C_1-C_6)$-alkoxy, and where heterocyclyl carries n oxo groups, Y represents hydrogen, nitro, halogen, cyano, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_6)$-cycloalkyl, $(C_3-C_6)$-cycloalkenyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $COOR^1$, $OCOOR^1$, $NR^1COOR^1$, $C(O)N(R^1)_2$, $NR^1C(O)N(R^1)_2$, $OC(O)N(R^1)_2$, $CO(NOR)R^1$, $CHNOR^1$, $CH_2ONC(R^3)_2$, $NR^1SO_2R^2$, $NR^1COR^1$, $OR^1$, $OSO_2R^2$, $S(O)_nR^2$, $SO_2OR^1$, $SO_2N(R^1)_2$ $(C_1-C_6)$-alkyl-$S(O)_nR^2$, $NS(O)R^8R^7$, $S(O)R^8NR^9$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-CN, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $N(R^1)_2$, $P(O)(OR^5)_2$, $CH_2P(O)(OR^5)_2$, $(C_1-C_6)$-alkylphenyl, $(C_1-C_6)$-alkylheteroaryl, $(C_1-C_6)$-alkylheterocyclyl, phenyl, heteroaryl or heterocyclyl, where the six last-mentioned radicals are each substituted by s radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy, $(C_1-C_6)$-alkoxy-$(C_1-C_4)$-alkyl and cyanomethyl, and where heterocyclyl carries n oxo groups, Z represents halogen, cyano, nitro, thiocyanato, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $COOR^1$, $OCOOR^1$, $NR^1COOR^1$, $C(O)N(R^1)_2$, $NR^1C(O)N(R^1)_2$, $OC(O)N(R^1)_2$, $C(O)NR^1OR^1$, $OSO_2R^2$, $S(O)_nR^2$, $SO_2OR^1$, $SO_2N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $N(R^1)_2$, $P(O)(OR^5)_2$, heteroaryl, heterocyclyl or phenyl, where the three last-mentioned radicals are each substituted by s radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy and halo-$(C_1-C_6)$-alkoxy, and where heterocyclyl carries n oxo groups, or Z may also represent hydrogen, $(C_1-C_6)$-alkyl or $(C_1-C_6)$-alkoxy if Y represents the $S(O)_nR^2$ radical, W represents hydrogen, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_7)$-cycloalkyl, $(C_3-C_7)$-halocycloalkyl, $(C_1-C_6)$-alkoxy, $(C_1-C_6)$-haloalkoxy, $S(O)_n$—$(C_1-C_6)$-alkyl, $S(O)_n$—$(C_1-C_6)$-haloalkyl, $(C_1-C_6)$-alkoxy-$(C_1-C_4)$-alkyl, $(C_1-C_6)$-alkoxy-$(C_1-C_4)$-haloalkyl, halogen, nitro, $NR^3COR^3$ or cyano, R represents $(C_1-C_8)$-alkyl, halo-$(C_1-C_8)$-alkyl, $(C_2-C_8)$-alkenyl, halo-$(C_2-C_8)$-alkenyl, $(C_2-C_8)$-alkynyl or halo-$(C_2-C_8)$-alkynyl, where these six abovementioned radicals are each substituted by s radicals from the group consisting of hydroxy, nitro, cyano, $SiR^5{}_3$, $PO(OR^5)_2$, $S(O)_n$—$(C_1-C_6)$-alkyl, $S(O)_n$—$(C_1-C_6)$-haloalkyl, $(C_1-C_6)$-alkoxy, halo-$(C_1-C_6)$-alkoxy, $N(R^3)_2$, $COR^3$, $COOR^3$, $OCOR^3$, $NR^3COR^3$, $NR^3SO_2R^4$, $O(C_1-C_2)$-alkyl-$(C_3-C_6)$-cycloalkyl, $(C_3-C_6)$-cycloalkyl, heteroaryl, heterocyclyl, phenyl, Q-heteroaryl, Q-heterocyclyl, Q-phenyl and Q-benzyl, where the seven last-mentioned radicals are each substituted by s radicals from the group consisting of methyl, ethyl, methoxy, trifluoromethyl, cyano and halogen, and where heterocyclyl carries n oxo groups, or R represents $(C_3-C_7)$-cycloalkyl, heteroaryl, heterocyclyl or phenyl, each of which is substituted by s radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy and $(C_1-C_6)$-alkoxy-$(C_1-C_4)$-alkyl, where heterocyclyl carries n oxo groups, Q represents O, S or $NR^3$, $R^1$ represents hydrogen, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl, $(C_3-C_6)$-cycloalkyl, $(C_3-C_6)$-cycloalkenyl, $(C_3-C_6)$-halocycloalkyl, $(C_1-C_6)$-alkyl-O—$(C_1-C_6)$-alkyl, $(C_3-C_6)$-cycloalkyl-$(C_1-C_6)$-alkyl, phenyl, phenyl-$(C_1-C_6)$-alkyl, heteroaryl, $(C_1-C_6)$-alkyl-heteroaryl, heterocycle, $(C_1-C_6)$-alkyl-heterocyclyl, $(C_1-C_6)$-alkyl-O-heteroaryl, $(C_1-C_6)$-alkyl-O-heterocyclyl, $(C_1-C_6)$-alkyl-$NR^3$-heteroaryl or $(C_1-C_6)$-alkyl-$NR^3$-heterocyclyl, where the 21 last-mentioned radicals are each substituted by s radicals from the group consisting of cyano, halogen, nitro, thiocyanato, $OR^3$, $S(O)_nR^4$, $N(R^3)_2$, $NR^3OR^3$, $COR^3$, $OCOR^3$, $SCOR^4$, $NR^3COR^3$, $NR^3SO_2R^4$, $CO_2R^3$, $COSR^4$, $CON(R^3)_2$ and $(C_1-C_4)$-alkoxy-$(C_2-C_6)$-alkoxycarbonyl, and where heterocyclyl carries n oxo groups, $R^2$ represents $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl, $(C_3-C_6)$-cycloalkyl, $(C_3-C_6)$-cycloalkenyl, $(C_3-C_6)$-halocycloalkyl, $(C_1-C_6)$-alkyl-O—$(C_1-C_6)$-alkyl, $(C_3-C_6)$-cycloalkyl-$(C_1-C_6)$-alkyl, phenyl, phenyl-$(C_1-C_6)$-alkyl, heteroaryl, $(C_1-C_6)$-alkylheteroaryl, heterocyclyl, $(C_1-C_6)$-alkylheterocyclyl, $(C_1-C_6)$-alkyl-O-heteroaryl, $(C_1-C_6)$-alkyl-O-heterocyclyl, $(C_1-C_6)$-alkyl-$NR^3$-heteroaryl or $(C_1-C_6)$-alkyl-$NR^3$-heterocyclyl, where the 21 last-mentioned radicals are each substituted by s radicals from the group consisting of cyano, halogen, nitro, thiocyanato, $OR^3$, $S(O)_nR^4$, $N(R^3)_2$, $NR^3OR^3$, $COR^3$, $OCOR^3$, $SCOR^4$, $NR^3COR^3$, $NR^3SO_2R^4$, $CO_2R^3$, $COSR^4$, $CON(R^3)_2$ and $(C_1-C_4)$-alkoxy-$(C_2-C_6)$-alkoxycarbonyl, and where heterocyclyl carries n oxo groups, $R^3$ represents hydrogen, $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl or phenyl, $R^4$ represents $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl or phenyl, $R^5$ represents $(C_1-C_4)$-alkyl, $R^6$ and $R^7$ each independently of one another represent $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $(C_1-C_6)$-alkoxy-$(C_1-C_6)$-alkyl, halo-$(C_1-C_6)$-alkoxy-$(C_1-C_6)$-alkyl, phenyl, heteroaryl or heterocyclyl, where the three last-mentioned radicals are each substituted by s radicals from the group consisting of nitro, halogen, cyano, thiocyanato, $(C_1-C_6)$-alkyl, halo-$(C_1-C_6)$-alkyl, $(C_3-C_6)$-cycloalkyl, $R^1O(O)C$, $(R^1)_2N(O)C$, $R^1O$, $(R^1)_2N$, $R^2(O)_nS$, $R^1O(O)_2S$, $(R^1)_2N(O)_2S$ and $R^1O$—$(C_1-C_6)$-alkyl, and where heterocyclyl carries n oxo groups, or $R^6$ and $R^7$ together with the sulfur atom to which they are bonded form a 3- to 8-membered unsaturated, semisaturated or saturated ring which contains, apart from the carbon atoms and apart from the sulfur atom of the sulfoximino group, in each case m ring members from the group consisting of $N(R^1)$, O and $S(O)_n$, and where this ring in each case is substituted by s radicals from the group consisting of nitro, halogen, cyano, thiocyanato, $(C_1-C_6)$-alkyl, halo-$(C_1-C_6)$-alkyl, $(C_3-C_6)$-cycloalkyl, $R^1O(O)C$, $(R^1)_2N(O)C$, $R^1O$, $(R^1)_2N$, $R^2(O)_nS$, $R^1O(O)_2S$, $(R^1)_2N(O)_2S$ and $R^1O$—$(C_1-C_6)$-alkyl, and where this ring bears n oxo groups, $R^8$ represents $(C_1-C_6)$-alkyl, $(C_2-C_6)$-alkenyl or $(C_2-C_6)$-alkynyl, each of which is substituted by s radicals from the group consisting of nitro, halogen, cyano, thiocyanato, $(C_3-C_6)$-cycloalkyl, $R^1(O)C$, $R^1(R^1ON=)C$, $R^1O(O)C$, $(R^1)_2N(O)C$, $R^1(R^1O)N(O)C$, $R^2(O)_2S(R^1)N(O)C$, $R^1O(O)_2S(R^1)N(O)C$, $(R^1)_2N(O)_2S(R^1)N(O)C$, $R^1S(O)C$, $R^1O$, $R^1(O)CO$, $R^2(O)_2SO$, $R^2O(O)CO$, $(R^1)_2N(O)CO$, $(R^1)_2N$, $R^1O(R^1)N$, $R^1(O)C(R^1)N$, $R^2(O)_2S(R^1)N$, $R^2O(O)C(R^1)N$, $(R^1)_2N(O)C(R^1)N$, $R^1O(O)_2S(R^1)N$, $(R^1)_2N(O)_2S(R^1)N$, $R^2(O)_nS$, $R^1C(O)S$, $R^1O(O)_2S$, $(R^1)_2N(O)_2S$, $R^1(O)C(R^1)N(O)_2S$, $R^2O(O)C(R^1)N(O)_2S$, $(R^1)_2N(O)C(R^1)N(O)_2S$ and $(R^6O)_2(O)P$, or $(C_3-C_6)$-cycloalkyl, $(C_3-C_6)$-cycloalkenyl, phenyl, phenyl-$(C_1-C_6)$-alkyl, heteroaryl, heteroaryl-$(C_1-C_6)$-alkyl, heterocyclyl, heterocyclyl-$(C_1-C_6)$-alkyl, phenyl-O—$(C_1-C_6)$-alkyl, heteroaryl-O—$(C_1-C_6)$-alkyl, heterocyclyl-O—$(C_1-C_6)$-alkyl, phenyl-$N(R^1)$—$(C_1-C_6)$-alkyl, heteroaryl-N$(R^1)$—$(C_1-C_6)$-alkyl, heterocyclyl-$N(R^1)$—$(C_1-C_6)$-alkyl, phenyl-$S(O)_n$—$(C_1-C_6)$-alkyl, heteroaryl-$S(O)_n$—$(C_1-C_6)$-alkyl or heterocyclyl-$S(O)_n$—$(C_1-C_6)$-alkyl, each of which is substituted in the cyclic moiety by s radicals from the group consisting of nitro, halogen, cyano, thiocyanato, $(C_1-C_6)$-alkyl, halo-$(C_1-C_6)$-alkyl, $(C_3-C_6)$-cycloalkyl, $R^1(O)C$, $R^1(R^1ON=)C$, $R^1O(O)C$, $(R^1)_2N(O)C$, $R^1(R^1O)N(O)C$, $R^2(O)_2S(R^1)N(O)C$, $R^1O(O)_2S(R^1)N(O)C$, $(R^1)_2N(O)_2S(R^1)N(O)C$, $R^1S(O)C$, $R^1O$, $R^1(O)CO$, $R_2(O)_2SO$, $R^2O(O)CO$, $(R^1)_2N(O)CO$, $(R^1)_2N$, $R^1O(R^1)N$, $R^1(O)C(R^1)N$, $R^2(O)_2S(R^1)N$, $R^2O(O)C(R^1)N$, $(R^1)_2N(O)C(R^1)N$, $R^1O(O)_2S(R^1)N$, $(R^1)_2N(O)_2S(R^1)N$, $R^2(O)_nS$, $R^1C(O)S$, $R^1O(O)_2S$, $(R^1)_2N(O)_2S$, $R^1(O)C(R^1)N(O)_2S$, $R^2O(O)C(R^1)N(O)_2S$, $(R^1)_2N(O)C(R^1)N(O)_2S$, $(R^5O)_2(O)P$ and $R^1O$—$(C_1-C_6)$-alkyl, and where heterocyclyl carries n oxo groups, $R^9$ represents hydrogen, nitro, halogen, cyano, $(C_1-C_6)$-alkyl, halo-$(C_1-C_6)$-alkyl, $(C_3-C_6)$-alkenyl, halo-$(C_3-C_6)$-alkenyl, $(C_2-C_6)$-alkynyl, halo-$(C_3-C_6)$-alkynyl, $(C_3-C_6)$-Cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $R^1(O)C$, $R^2O(O)C$, $(R^1)_2N(O)C$, $R^2S(O)C$, $(R^1)_2N(S)C$, $R^1(R^1O)N(O)C$, $R^2(O)_2S(R^1)N(O)C$, $(R^1)_2N(O)_2S(R^1)N(O)C$, $R^1O$, $(R^1)_2N$, $R^2(O)_nS$, $(R^2)_3Si$—$(C_1-C_6)$-alkyl-$(O)_nS$, $R^1O(O)_2S$, $(R^1)_2N(O)_2S$, $R^1(O)C(R^1)N(O)_2S$, $R^2O(O)C(R^1)N(O)_2S$, $(R^1)_2N(O)C(R^1)N(O)_2S$, $R^2(O)_2S(R^1)N(O)_2S$, $(R^5O)_2(O)P$, $(R^2)_3Si$, $R^1(O)C$—$(C_1-C_6)$-alkyl, $R^1O(O)C$—$(C_1-C_6)$-alkyl, $(R^1)_2N(O)C$—$(C_1-C_6)$-alkyl, $(R^1O)(R^1)N(O)C$—$(C_1-C_6)$-alkyl, $R^2(O)_2S(R^1)N(O)C$—$(C_1-C_6)$-alkyl, $R^1O(O)_2S(R^1)N(O)C$—$(C_1-C_6)$-alkyl, $(R^1)_2N(O)_2S(R^1)N(O)C$—$(C_1-C_6)$-alkyl, $R^1O$—$(C_1-C_6)$-alkyl, $R^1(O)CO$—$(C_1-C_6)$-alkyl, $R^2(O)_2SP$—$(C_1-C_6)$-alkyl, $R^2O(O)CO$—$(C_1-C_6)$-alkyl, $(R^1)_2N(O)CO$—$(C_1-C_6)$-alkyl, $(R^1)_2N$—$(C_1-C_6)$-alkyl, $R^1(O)C(R^1)N$—$(C_1-C_6)$-alkyl, $R^2(O)_2S(R^1)N$—$(C_1-C_6)$-alkyl, $R^2O(O)C(R^1)N$—$(C_1-C_6)$-alkyl, $(R^1)_2N(O)C(R^1)N$—$(C_1-C_6)$-alkyl, $R^1O(O)_2S(R^1)N$—$(C_1-C_6)$-alkyl, $(R^1)_2N(O)_2S(R^1)N$—$(C_1-C_6)$-alkyl, $R^2(O)_nS$—$(C_1-C_6)$-alkyl, $R^1O(O)_2S$—$(C_1-C_6)$-alkyl, $(R^1)_2N(O)_2S$—$(C_1-C_6)$-alkyl, $R^1(O)C(R^1)N(O)_2S$—$(C_1-C_6)$-alkyl, $R^2O(O)C(R^1)N(O)_2S$—$(C_1-C_6)$-alkyl, $(R^1)_2N(O)C(R^1)N(O)_2S$—$(C_1-C_6)$-alkyl, $(R^5O)_2(O)P$—$(C_1-C_6)$-alkyl, $(R^2)_3Si$—$(C_1-C_6)$-alkyl, or phenyl, heteroaryl, heterocyclyl, phenyl-$(C_1-C_6)$-alkyl, heteroaryl-$(C_1-C_6)$-alkyl or heterocyclyl-$(C_1-C_6)$-alkyl, each of which is substituted in the cyclic moiety by s radicals from the group consisting of nitro, halogen, cyano, thiocyanato, $(C_1-C_6)$-alkyl, halo-$(C_1-C_6)$-alkyl, $(C_3-C_6)$-cycloalkyl, $R^1O(O)C$, $(R^1)_2N(O)C$, $R^1O$, $(R^1)_2N$, $R^2(O)_nS$, $R^1O(O)_2S$, $(R^1)_2N(O)_2S$ and $R^1O$—$(C_1-C_6)$-alkyl, and where heterocyclyl carries n oxo groups, m represents 0, 1, 2, 3 or 4,
n represents 0, 1 or 2,
s represents 0, 1, 2 or 3.

DETAILED DESCRIPTION OF A PREFERRED EMBODIMENT

In the formula (I) and all the formulae which follow, alkyl radicals having more than two carbon atoms may be straight-chain or branched. Alkyl radicals represent, for example, methyl, ethyl, n- or isopropyl, n-, iso-, tert- or 2-butyl, pentyls, hexyls such as n-hexyl, isohexyl and 1,3-dimethylbutyl. Analogously, alkenyl represents, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl. Alkynyl represents, for example, propargyl, but-2-yn-1-yl, but-3-yn-1-yl, 1-methylbut-3-yn-1-yl. The multiple bond may be in each case in any position of the unsaturated radical. Cycloalkyl represents a carbocyclic saturated ring system having three to six carbon atoms, for example cyclopropyl, cyclobutyl, cyclopentyl or cyclohexyl. Analogously, cycloalkenyl represents a monocyclic alkenyl group having three to six carbon ring members, for example cyclopropenyl, cyclobutenyl, cyclopentenyl and cyclohexenyl, where the double bond may be in any position.

Halogen represents fluorine, chlorine, bromine or iodine.

Heterocyclyl represents a saturated, semisaturated or fully unsaturated cyclic radical containing 3 to 6 ring atoms, of which 1 to 4 are from the group consisting of oxygen, nitrogen and sulfur, and which may additionally be fused by a benzo ring. For example, heterocyclyl represents piperidinyl, pyrrolidinyl, tetrahydrofuranyl, dihydrofuranyl and oxetanyl.

Heteroaryl represents an aromatic cyclic radical containing 3 to 6 ring atoms, of which 1 to 4 are from the group consisting of oxygen, nitrogen and sulfur, and which may additionally be fused by a benzo ring. For example, heteroaryl represents benzimidazol-2-yl, furanyl, imidazolyl, isoxazolyl, isothiazolyl, oxazolyl, pyrazinyl, pyrimidinyl, pyridazinyl, pyridinyl, benzisoxazolyl, thiazolyl, pyrrolyl, pyrazolyl, thiophenyl, 1,2,3-oxadiazolyl, 1,2,4-oxadiazolyl, 1,2,5-oxadiazolyl, 1,3,4-oxadiazolyl, 1,2,4-triazolyl, 1,2,3-triazolyl, 1,2,5-triazolyl, 1,3,4-triazolyl, 1,2,4-triazolyl, 1,2,4-thiadiazolyl, 1,3,4-thiadiazolyl, 1,2,3-thiadiazolyl, 1,2,5-thiadiazolyl, 2H-1,2,3,4-tetrazolyl, 1H-1,2,3,4-tetrazolyl, 1,2,3,4-oxatriazolyl, 1,2,3,5-oxatriazolyl, 1,2,3,4-thiatriazolyl and 1,2,3,5-thiatriazolyl.

When a group is polysubstituted by radicals, this means that this group is substituted by one or more identical or different radicals from those mentioned. This applies analogously to the formation of ring systems by various atoms and elements. At the same time, the scope of the claims shall exclude those compounds known to the person skilled in the art to be chemically unstable under standard conditions.

Depending on the nature of the substituents and manner in which they are attached, the compounds of the general formula (I) may be present as stereoisomers. If, for example, one or more asymmetric carbon atoms are present, there may be enantiomers and diastereomers. Stereoisomers likewise occur when n represents 1 (sulfoxides). Stereoisomers can be obtained from the mixtures obtained in the preparation by customary separation methods, for example by chromatographic separation processes. It is likewise possible to selectively prepare stereoisomers by using stereoselective reactions with use of optically active starting materials and/or auxiliaries. The invention also relates to all stereoisomers and mixtures thereof which are encompassed by the general formula (I) but not defined specifically.

The compounds of the formula (I) may form salts. Salts may be formed by action of a base on compounds of the formula (I). Examples of suitable bases are organic amines such as trialkylamines, morpholine, piperidine and pyridine, and the hydroxides, carbonates and hydrogencarbonates of ammonium, alkali metals or alkaline earth metals, in particular sodium hydroxide, potassium hydroxide, sodium carbonate, potassium carbonate, sodium hydrogencarbonate and potassium hydrogencarbonate. These salts are compounds in which the acidic hydrogen is replaced by an agriculturally suitable cation, for example metal salts, in particular alkali metal salts or alkaline earth metal salts, in particular sodium and potassium salts, or else ammonium salts, salts with organic amines or quaternary ammonium salts, for example with cations of the formula $[NR^aR^bR^cR^d]^+$, in which $R^a$ to $R^d$ in each case independently of one another represent an organic radical, in particular alkyl, aryl, aralkyl or alkylaryl. Also useful are alkylsulfonium and alkylsulfoxonium salts, such as $(C_1-C_4)$-trialkylsulfonium and $(C_1-C_4)$-trialkylsulfoxonium salts.

The compounds of the formula (I) can form salts by addition of a suitable inorganic or organic acid, for example mineral acids, for example HCl, HBr, $H_2SO_4$, $H_3PO_4$ or $HNO_3$, or organic acids, for example carboxylic acids such as formic acid, acetic acid, propionic acid, oxalic acid, lactic acid or salicylic acid, or sulfonic acids, for example p-toluenesulfonic acid, onto a basic group, for example amino, alkylamino, dialkylamino, piperidino, morpholino or pyridino.

Preference is given to compounds of the general formula (I) in which

A represents N or CY,
B represents N or CH,
X represents nitro, halogen, cyano, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3-C_6)$-cycloalkyl, $(C_1-C_6)$-alkyl-O—$(C_1-C_6)$-alkyl, $(C_3-C_6)$-cycloalkyl-$(C_1-C_6)$-alkyl, halo-$(C_3-C_6)$-cycloalkyl-$(C_1-C_6)$-alkyl, $COR^1$, $OR^1$, $OCOR^1$, $OSO_2R^2$, $S(O)_nR^2$, $SO_2OR^1$, $SO_2N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$ or $(C_1-C_6)$-alkyl-$NR^1SO_2R^2$, $(C_1-C_6)$-alkyl-heteroaryl or $(C_1-C_6)$-alkyl-heterocyclyl, where the two last-mentioned radicals are each substituted by s radicals from the group consisting of halogen, $(C_1-C_6)$-alkyl, halo-$(C_1-C_6)$-alkyl, $S(O)_n$—$(C_1-C_6)$-alkyl, $(C_1-C_6)$-alkoxy and halo-$(C_1-C_6)$-alkoxy, and where heterocyclyl carries n oxo groups, Y represents hydrogen, nitro, halogen, cyano, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, $(C_3-C_6)$-cycloalkenyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $OR^1$, $COOR^1$, $CHNOR^1$, $CH_2ONC(R^3)_2$, $OSO_2R^2$, $S(O)_nR^2$, $SO_2OR^1$, $SO_2N(R^1)_2$, $NS(O)R^6R^7$, $S(O)R^8NR^9$, $N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$- alkyl-CO$_2$R$^1$, (C$_1$-C$_6$)-alkyl-SO$_2$OR$^1$, (C$_1$-C$_6$)-alkyl-CON(R$^1$)$_2$, (C$_1$-C$_6$)-alkyl-SO$_2$N(R$^1$)$_2$, (C$_1$-C$_6$)-alkyl-NR$^1$COR$^1$, (C$_1$-C$_6$)-alkyl-NR$^1$SO$_2$R$^2$, (C$_1$-C$_6$)-alkyl-phenyl, (C$_1$-C$_6$)-alkyl-heteroaryl, (C$_1$-C$_6$)-alkyl-heterocyclyl, phenyl, heteroaryl or heterocyclyl, where the six last-mentioned radicals are each substituted by s radicals from the group consisting of halogen, nitro, cyano, (C$_1$-C$_6$)-alkyl, halo-(C$_1$-C$_6$)-alkyl, (C$_3$-C$_6$)-cycloalkyl, S(O)$_n$—(C$_1$-C$_6$)-alkyl, (C$_1$-C$_6$)-alkoxy, halo-(C$_1$-C$_6$)-alkoxy, (C$_1$-C$_6$)-alkoxy-(C$_1$-C$_4$)-alkyl and cyanomethyl, and where heterocyclyl carries n oxo groups, Z represents halogen, cyano, nitro, thiocyanato, halo-(C$_1$-C$_6$)-alkyl, (C$_2$-C$_6$)-alkenyl, halo-(C$_2$-C$_6$)-alkenyl, (C$_2$-C$_6$)-alkynyl, halo-(C$_3$-C$_6$)-alkynyl, (C$_3$-C$_6$)-cycloalkyl, halo-(C$_3$-C$_6$)-cycloalkyl, (C$_3$-C$_6$)-cycloalkyl-(C$_1$-C$_6$)-alkyl, halo-(C$_3$-C$_6$)-cycloalkyl-(C$_1$-C$_6$)-alkyl, COR$^1$, COOR$^1$, C(O)N(R$^1$)$_2$, C(O)NR$^1$OR$^1$, OSO$_2$R$^2$, S(O)$_n$R$^2$, SO$_2$OR$^1$, SO$_2$N(R$^1$)$_2$, NR$^1$SO$_2$R$^2$, NR$^1$COR$^1$, (C$_1$-C$_6$)-alkyl-S(O)$_n$R$^2$, (C$_1$-C$_6$)-alkyl-OR$^1$, (C$_1$-C$_6$)-alkyl-OCOR$^1$, (C$_1$-C$_6$)-alkyl-OSO$_2$R$^2$, (C$_1$-C$_6$)-alkyl-CO$_2$R$^1$, (C$_1$-C$_6$)-alkyl-SO$_2$OR$^1$, (C$_1$-C$_6$)-alkyl-CON(R$^1$)$_2$, (C$_1$-C$_6$)-alkyl-SO$_2$N(R$^1$)$_2$, (C$_1$-C$_6$)-alkyl-NR$^1$COR$^1$, (C$_1$-C$_6$)-alkyl-NR$^1$SO$_2$R$^2$ or 1,2,4-triazol-1-yl, or Z may also represent hydrogen, (C$_1$-C$_6$)-alkyl or (C$_1$-C$_6$)-alkoxy if Y represents the S(O)$_n$R$^2$ radical, W represents hydrogen, (C$_1$-C$_6$)-alkyl, halo-(C$_1$-C$_6$)-alkyl, (C$_1$-C$_6$)-alkoxy, (C$_1$-C$_6$)-haloalkoxy, S(O)$_n$—(C$_1$-C$_6$)-alkyl, S(O)$_n$—(C$_1$-C$_6$)-haloalkyl, (C$_1$-C$_6$)-alkoxy-(C$_1$-C$_4$)-alkyl, halogen, nitro or cyano, R represents (C$_1$-C$_6$-alkyl, halo-(C$_1$-C$_6$-alkyl, (C$_2$-C$_6$)-alkenyl, halo-(C$_2$-C$_8$)-alkenyl, (C$_2$-C$_8$)-alkynyl, halo-(C$_2$-C$_8$)-alkynyl, where these six abovementioned radicals are each substituted by s radicals from the group consisting of nitro, cyano, SiR$^5$$_3$, P(OR$^5$)$_3$, S(O)$_n$—(C$_1$-C$_6$)-alkyl, (C$_1$-C$_6$)-alkoxy, halo-(C$_1$-C$_6$)-alkoxy, N(R$^3$)$_2$, COR$^3$, COOR$^3$, OCOR$^3$, NR$^3$COR$^3$, NR$^3$SO$_2$R$^4$, (C$_3$-C$_6$)-cycloalkyl, heteroaryl, heterocyclyl, phenyl, Q-heteroaryl, Q-heterocyclyl, Q-phenyl and Q-benzyl, where the seven last-mentioned radicals are each substituted by s radicals from the group consisting of methyl, ethyl, methoxy, trifluoromethyl, cyano and halogen, and where heterocyclyl carries n oxo groups, or R represents (C$_3$-C$_7$)-cycloalkyl, heteroaryl, heterocyclyl or phenyl, each of which is substituted by s radicals from the group consisting of halogen, nitro, cyano, (C$_1$-C$_6$)-alkyl, halo-(C$_1$-C$_6$)-alkyl, (C$_3$-C$_6$)-cycloalkyl, S(O)$_n$—(C$_1$-C$_6$)-alkyl, (C$_1$-C$_6$)-alkoxy, halo-(C$_1$-C$_6$)-alkoxy and (C$_1$-C$_6$)-alkoxy-(C$_1$-C$_4$)-alkyl, Q represents O, S or NR$^3$, R$^1$ represents hydrogen, (C$_1$-C$_6$)-alkyl, (C$_2$-C$_6$)-alkenyl, (C$_2$-C$_6$)-alkynyl, (C$_3$-C$_6$)-cycloalkyl, (C$_3$-C$_6$)-cycloalkyl-(C$_1$-C$_6$)-alkyl, (C$_1$-C$_6$)-alkyl-O—(C$_1$-C$_6$)-alkyl, phenyl, phenyl-(C$_1$-C$_6$)-alkyl, heteroaryl, (C$_1$-C$_6$)-alkylheteroaryl, heterocyclyl, (C$_1$-C$_6$)-alkylheterocyclyl, (C$_1$-C$_6$)-alkyl-O-heterocyclyl, (C$_1$-C$_6$)-alkyl-O-heterocyclyl, (C$_1$-C$_6$)-alkyl-NR$^3$-heteroaryl or (C$_1$-C$_6$)-alkyl-NR$^3$-heterocyclyl, where the sixteen last-mentioned radicals are each substituted by s radicals from the group consisting of cyano, halogen, nitro, OR$^3$, S(O)$_n$R$^4$, N(R$^3$)$_2$, NR$^3$OR$^3$, COR$^3$, OCOR$^3$, NR$^3$COR$^3$, NR$^3$SO$_2$R$^4$, CO$_2$R$^3$, CON(R$^3$)$_2$ and (C$_1$-C$_4$)-alkoxy-(C$_2$-C$_6$)-alkoxycarbonyl, and where heterocyclyl carries n oxo groups, R$^2$ represents (C$_1$-C$_6$)-alkyl, (C$_2$-C$_6$)-alkenyl, (C$_2$-C$_6$)-alkynyl, (C$_3$-C$_6$)-cycloalkyl, (C$_3$-C$_6$)-cycloalkyl-(C$_1$-C$_6$)-alkyl, (C$_1$-C$_6$)-alkyl-O—(C$_1$-C$_6$)-alkyl, phenyl, phenyl-(C$_1$-C$_6$)-alkyl, heteroaryl, (C$_1$-C$_6$)-alkylheteroaryl, heterocyclyl, (C$_1$-C$_6$)-alkylheterocyclyl, (C$_1$-C$_6$)-alkyl-O-heterocyclyl, (C$_1$-C$_6$)-alkyl-O-heterocyclyl, (C$_1$-C$_6$)-alkyl-NR$^3$-heteroaryl or (C$_1$-C$_6$)-alkyl-NR$^3$-heterocyclyl, where these sixteen last-mentioned radicals are each substituted by s radicals from the group consisting of cyano, halogen, nitro, OR$^3$, S(O)$_n$R$^4$, N(R$^3$)$_2$, NR$^3$OR$^3$, NR$^3$SO$_2$R$^4$, COR$^3$, OCOR$^3$, NR$^3$COR$^3$, CO$_2$R$^3$, CON(R$^3$)$_2$ and (C$_1$-C$_4$)-alkoxy-(C$_2$-C$_6$)-alkoxycarbonyl, and where heterocyclyl carries n oxo groups, R$^3$ represents hydrogen, (C$_1$-C$_6$)-alkyl, (C$_2$-C$_6$)-alkenyl, (C$_2$-C$_6$)-alkynyl, (C$_3$-C$_6$)-cycloalkyl or (C$_3$-C$_6$)-cycloalkyl-(C$_1$-C$_6$)-alkyl, R$^4$ represents (C$_1$-C$_6$)-alkyl, (C$_2$-C$_6$)-alkenyl or (C$_2$-C$_6$)-alkynyl, R$^5$ represents methyl or ethyl, R$^6$ and R$^7$ each independently of one another represent (C$_1$-C$_6$)-alkyl, halo-(C$_1$-C$_6$)-alkyl, (C$_3$-C$_6$)-cycloalkyl, halo-(C$_3$-C$_6$)-cycloalkyl, (C$_3$-C$_6$)-cycloalkyl-(C$_1$-C$_6$)-alkyl, halo-(C$_3$-C$_6$)-cycloalkyl-(C$_1$-C$_6$)-alkyl, (C$_1$-C$_6$)-alkoxy-(C$_1$-C$_6$)-alkyl, halo-(C$_1$-C$_6$)-alkoxy-(C$_1$-C$_6$)-alkyl, phenyl, heteroaryl or heterocyclyl, where the three last-mentioned radicals are each substituted by s radicals from the group consisting of nitro, halogen, (C$_1$-C$_6$)-alkyl, halo-(C$_1$-C$_6$)-alkyl, R$^1$O(O)C, (R$^1$)$_2$N(O)C, R$^1$O, (R$^1$)$_2$N, R$^2$(O)$_n$S and R$^1$O—(C$_1$-C$_6$)-alkyl, and where heterocyclyl carries n oxo groups, or R$^6$ and R$^7$ together with the sulfur atom to which they are attached form a 3- to 8-membered unsaturated, partially saturated or saturated ring which contains, in addition to the carbon atoms and in addition to the sulfur atom of the sulfoximino group, in each case m ring members from the group consisting of N(R$^1$), O and S(O)$_n$, and where this ring is in each case substituted by s radicals from the group consisting of halogen, (C$_1$-C$_6$)-alkyl, halo-(C$_1$-C$_6$)-alkyl, R$^1$O(O)C, (R$^1$)$_2$N(O)C, R$^1$O, (R$^1$)$_2$N, R$^2$(O)$_n$S, R$^1$O(O)$_2$S, (R$^1$)$_2$N(O)$_2$S and R$^1$O—(C$_1$-C$_6$)-alkyl, and where this ring carries n oxo groups, R$^8$ represents (C$_1$-C$_6$)-alkyl which is in each case substituted by s radicals from the group consisting of halogen, cyano, (C$_3$-C$_6$)-cycloalkyl, R$^1$(O)C, R$^1$(R$^1$ON═)C, R$^1$O(O)C, (R$^1$)$_2$N(O)C, R$^2$(O)$_2$S(R$^1$)N(O)C, R$^1$O, (R$^1$)$_2$N, R$^1$(O)C(R$^1$)N, R$^2$(O)$_2$S(R$^1$)N, R$^2$O(O)C(R$^1$)N, (R$^1$)$_2$N(O)C(R$^1$)N, R$^2$(O)$_n$S, R$^1$O(O)$_2$S, (R$^1$)$_2$N(O)$_2$S, R$^1$(O)C(R$^1$)N(O)$_2$S, R$^2$O(O)C(R$^1$)N(O)$_2$S and (R$^1$)$_2$N(O)C(R$^1$)N(O)$_2$S or (C$_3$-C$_6$)-cycloalkyl which is in each case substituted by s radicals from the group consisting of halogen, (C$_1$-C$_6$)-alkyl, halo-(C$_1$-C$_6$)-alkyl, (C$_3$-C$_6$)-cycloalkyl, R$^1$O(O)C and (R$^1$)$_2$N(O)C, R$^9$ represents hydrogen, nitro, cyano, (C$_1$-C$_6$)-alkyl, halo-(C$_1$-C$_6$)-alkyl, (C$_3$-C$_6$)-cycloalkyl, halo-(C$_3$-C$_6$)-cycloalkyl, (C$_3$-C$_6$)-cycloalkyl-(C$_1$-C$_6$)-alkyl, halo-(C$_3$-C$_6$)-cycloalkyl-(C$_1$-C$_6$)-alkyl, R$^1$(O)C, R$^2$O(O)C, (R$^1$)$_2$N(O)C, R$^2$(O)$_2$S, R$^1$(O)C—(C$_1$-C$_6$)-alkyl, R$^1$O(O)C—(C$_1$-C$_6$)-alkyl, (R$^1$)$_2$N(O)C—(C$_1$-C$_6$)-alkyl, R$^1$O—(C$_1$-C$_6$)-alkyl, (R$^1$)$_2$N—(C$_1$-C$_6$)-alkyl or R$^2$(O)$_n$S—(C$_1$-C$_6$)-alkyl, m represents 0, 1 or 2, n represents 0, 1 or 2, s represents 0, 1, 2 or 3.

Particular preference is given to compounds of the general formula (I) in which

A represents N or CY,

B represents N or CH,

X represents nitro, halogen, cyano, (C$_1$-C$_6$)-alkyl, halo-(C$_1$-C$_6$)-alkyl, (C$_3$-C$_6$)-cycloalkyl, OR$^1$, S(O)$_n$R$^2$, (C$_1$-C$_6$)-alkyl-S(O)$_n$R$^2$, (C$_1$-C$_6$)-alkyl-OR$^1$, (C$_1$-C$_6$)-alkyl-CON(R$^1$)$_2$, (C$_1$-C$_6$)-alkyl-SO$_2$N(R$^1$)$_2$, (C$_1$-C$_6$)-alkyl-NR$^1$COR$^1$, (C$_1$-C$_6$)-alkyl-NR$^1$SO$_2$R$^2$, (C$_1$-C$_6$)-alkylheteroaryl or (C$_1$-C$_6$)-alkylheterocyclyl, where the two last-mentioned radicals are each substituted by s halogen, (C$_1$-C$_6$)-alkyl, halo- ($C_1$-$C_6$)-alkyl, $S(O)_n$—($C_1$-$C_6$)-alkyl, ($C_1$-$C_6$)-alkoxy and halo-($C_1$-$C_6$)-alkoxy radicals, and where heterocyclyl carries n oxo groups, Y hydrogen, nitro, halogen, cyano, ($C_1$-$C_6$)-alkyl, ($C_1$-$C_6$)-haloalkyl, $OR^1$, $S(O)_n R^2$, $SO_2 N(R^1)_2$, $NS(O)R^6 R^7$, $S(O)R^8 NR^9$, $N(R^1)_2$, $CHNOR^1$, $CH_2 ONC(R^3)_2$, $NR^1 SO_2 R^2$, $NR^1 COR^1$, ($C_1$-$C_6$)-alkyl-$S(O)_n R^2$, ($C_1$-$C_6$)-alkyl-$OR^1$, ($C_1$-$C_6$)-alkyl-$CON(R^1)_2$, ($C_1$-$C_6$)-alkyl-$SO_2 N(R^1)_2$, ($C_1$-$C_6$)-alkyl-$NR^1 COR^1$, ($C_1$-$C_6$)-alkyl-$NR^1 SO_2 R^2$, ($C_1$-$C_6$)-alkyl-phenyl, ($C_1$-$C_6$)-alkyl-heteroaryl, ($C_1$-$C_6$)-alkyl-heterocyclyl, phenyl, heteroaryl or heterocyclyl, where the six last-mentioned radicals are each substituted by s radicals from the group consisting of halogen, nitro, cyano, ($C_1$-$C_6$)-alkyl, halo-($C_1$-$C_6$)-alkyl, ($C_3$-$C_6$)-cycloalkyl, $S(O)_n$—($C_1$-$C_6$)-alkyl, ($C_1$-$C_6$)-alkoxy, halo-($C_1$-$C_6$)-alkoxy, ($C_1$-$C_6$)-alkoxy-($C_1$-$C_4$)-alkyl and cyanomethyl, and where heterocyclyl carries n oxo groups, Z represents halogen, cyano, halo-($C_1$-$C_6$)-alkyl, ($C_3$-$C_6$)-cycloalkyl, $S(O)_n R^2$, 1,2,4-triazol-1-yl, or Z may also represent hydrogen, methyl, methoxy or ethoxy if Y represents the $S(O)_n R^2$ radical, W represents hydrogen, methyl, ethyl, methoxymethyl, methoxy, fluorine, chlorine or $S(O)_n CH_3$, R represents ($C_1$-$C_8$)-alkyl, halo-($C_1$-$C_8$)-alkyl, ($C_2$-$C_8$)-alkenyl, halo-($C_2$-$C_8$)-alkenyl, ($C_2$-$C_8$)-alkynyl, halo-($C_2$-$C_8$)-alkynyl, where these six abovementioned radicals are each substituted by s radicals from the group consisting of cyano, $S(O)_n$—($C_1$-$C_6$)-alkyl, ($C_1$-$C_6$)-alkoxy, halo-($C_1$-$C_6$)-alkoxy, $COR^3$, $COOR^3$, $OCOR^3$, $NR^3 COR^3$, $NR^3 SO_2 R^4$, ($C_3$-$C_6$)-cycloalkyl, heteroaryl, heterocyclyl and phenyl, where the three last-mentioned radicals are each substituted by s radicals from the group consisting of methyl, ethyl, methoxy, trifluoromethyl, cyano and halogen, and where heterocyclyl carries 0 to 2 oxo groups, or R represents phenyl which is substituted by s radicals from the group consisting of halogen, nitro, cyano, ($C_1$-$C_6$)-alkyl, halo-($C_1$-$C_6$)-alkyl, ($C_3$-$C_6$)-cycloalkyl, $S(O)_n$—($C_1$-$C_6$)-alkyl, ($C_1$-$C_6$)-alkoxy, halo-($C_1$-$C_6$)-alkoxy and ($C_1$-$C_6$)-alkoxy-($C_1$-$C_4$)-alkyl, $R^1$ represents hydrogen, ($C_1$-$C_6$)-alkyl, ($C_2$-$C_6$)-alkenyl, ($C_2$-$C_6$)-alkynyl, ($C_3$-$C_6$)-cycloalkyl, ($C_3$-$C_6$)-cycloalkyl-($C_1$-$C_6$)-alkyl, ($C_1$-$C_6$)-alkyl-O—($C_1$-$C_6$)-alkyl, phenyl, phenyl-($C_1$-$C_6$)-alkyl, heteroaryl, ($C_1$-$C_6$)-alkylheteroaryl, heterocyclyl, ($C_1$-$C_6$)-alkylheterocyclyl, ($C_1$-$C_6$)-alkyl-O-heteroaryl, ($C_1$-$C_6$)-alkyl-O-heterocyclyl, ($C_1$-$C_6$)-alkyl-$NR^3$-heteroaryl or ($C_1$-$C_6$)-alkyl-$NR^3$-heterocyclyl, where the sixteen last-mentioned radicals are each substituted by s radicals from the group consisting of cyano, halogen, nitro, $OR^3$, $S(O)_n R^4$, $N(R^3)_2$, $NR^3 OR^3$, $COR^3$, $OCOR^3$, $NR^3 COR^3$, $NR^3 SO_2 R^4$, $CO_2 R^3$, $CON(R^3)_2$ and ($C_1$-$C_4$)-alkoxy-($C_2$-$C_6$)-alkoxycarbonyl, and where heterocyclyl carries n oxo groups, $R^2$ represents ($C_1$-$C_6$)-alkyl, ($C_3$-$C_6$)-cycloalkyl or ($C_3$-$C_6$)-cycloalkyl-($C_1$-$C_6$)-alkyl, each substituted by s radicals from the group consisting of halogen and $OR^3$, $R^3$ represents hydrogen or ($C_1$-$C_6$)-alkyl, $R^4$ represents ($C_1$-$C_6$)-alkyl, $R^6$ and $R^7$ independently of one another each represent methyl, ethyl or n-propyl, or $R^6$ and $R^7$ together with the sulfur atom to which they are attached form a 5- or 6-membered saturated ring which, in addition to the carbon atoms and in addition to the sulfur atom of the sulfoximino group, contains m oxygen atoms, $R^8$ represents methyl, ethyl or n-propyl, $R^9$ represents hydrogen or cyano, m represents 0 or 1, n represents 0, 1 or 2, s represents 0, 1, 2 or 3.

In all the formulae specified hereinafter, the substituents and symbols have the same meaning as described in formula (I), unless defined differently.

Compounds according to the invention can be prepared, for example, by the method indicated in Scheme 1 by reacting an N-(tetrazol-5-yl)- and N-(triazol-5-yl)benzamide and nicotinamide (II) with a sulfurizing agent such as, for example, phosphorus pentasulfide or Lawesson's reagent:

Scheme 1

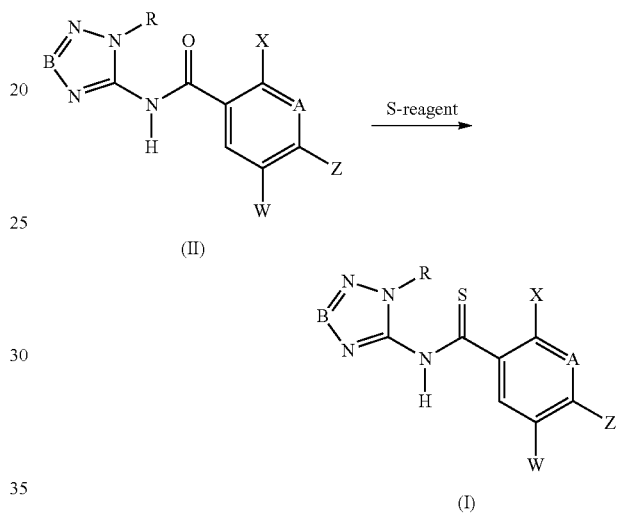

The N-(tetrazol-5-yl)- and N-(triazol-5-yl)benzamides and nicotinamides of the formula (II) can be prepared, for example, by the methods described in WO 2012/028579 A1, EP 11158253 and EP 11159115.

It may be expedient to change the order of reaction steps. Thus, benzoic acids carrying a sulfoxide cannot be converted directly into their acid chlorides. Here, it is advisable to prepare initially, at the thioether stage, the amide and then to oxidize the thioether to the sulfoxide.

Collections of compounds of the formula (I) and/or salts thereof which can be synthesized by the abovementioned reactions can also be prepared in a parallelized manner, in which case this may be accomplished in a manual, partly automated or fully automated manner. It is possible, for example, to automate the conduct of the reaction, the work-up or the purification of the products and/or intermediates. Overall, this is understood to mean a procedure as described, for example, by D. Tiebes in Combinatorial Chemistry—Synthesis, Analysis, Screening (editor Günther Jung), Wiley, 1999, on pages 1 to 34.

For the parallelized conduct of the reaction and workup, it is possible to use a number of commercially available instruments, for example Calypso reaction blocks from Barnstead International, Dubuque, Iowa 52004-0797, USA or reaction stations from Radleys, Shirehill, Saffron Walden, Essex, CB11 3AZ, England, or MultiPROBE Automated Workstations from PerkinElmer, Waltham, Mass. 02451, USA. For the parallelized purification of compounds of the general formula (I) and salts thereof or of intermediates which occur in the course of preparation, available apparatuses include chromatography apparatuses, for example from ISCO, Inc., 4700 Superior Street, Lincoln, Nebr. 68504, USA.

The apparatuses detailed lead to a modular procedure in which the individual working steps are automated, but manual operations have to be carried out between the working steps. This can be circumvented by using partly or fully integrated automation systems in which the respective automation modules are operated, for example, by robots. Automation systems of this type can be obtained, for example, from Caliper, Hopkinton, Mass. 01748, USA.

The implementation of single or multiple synthesis steps can be supported by the use of polymer-supported reagents/scavenger resins. The specialist literature describes a series of experimental protocols, for example in ChemFiles, Vol. 4, No. 1, Polymer-Supported Scavengers and Reagents for Solution-Phase Synthesis (Sigma-Aldrich).

Aside from the methods described here, the compounds of the general formula (I) and salts thereof can be prepared completely or partially by solid-phase-supported methods. For this purpose, individual intermediates or all intermediates in the synthesis or a synthesis adapted for the corresponding procedure are bound to a synthesis resin. Solid-phase-supported synthesis methods are described adequately in the technical literature, for example Barry A. Bunin in "The Combinatorial Index", Academic Press, 1998 and Combinatorial Chemistry—Synthesis, Analysis, Screening (editor Gunther Jung), Wiley, 1999. The use of solid-phase-supported synthesis methods permits a number of protocols, which are known from the literature and which for their part may be performed manually or in an automated manner. The reactions can be performed, for example, by means of IRORI technology in microreactors from Nexus Biosystems, 12140 Community Road, Poway, Calif. 92064, USA.

Both in the solid and in the liquid phase, individual or several synthesis steps may be supported by the use of microwave technology. The specialist literature describes a series of experimental protocols, for example in Microwaves in Organic and Medicinal Chemistry (editor C. O. Kappe and A. Stadler), Wiley, 2005.

The preparation by the processes described here gives compounds of the formula (I) and salts thereof in the form of substance collections, which are called libraries. The present invention also provides libraries comprising at least two compounds of the formula (I) and salts thereof.

The compounds of the formula (I) according to the invention (and/or salts thereof), collectively referred to hereinafter as "compounds according to the invention", have excellent herbicidal efficacy against a broad spectrum of economically important monocotyledonous and dicotyledonous annual harmful plants. The active compounds also have good control over perennial harmful plants which are difficult to control and produce shoots from rhizomes, root stocks or other perennial organs.

The present invention therefore also provides a method for controlling unwanted plants or for regulating the growth of plants, preferably in plant crops, in which one or more compound(s) according to the invention is/are applied to the plants (for example harmful plants such as monocotyledonous or dicotyledonous weeds or unwanted crop plants), the seed (for example grains, seeds or vegetative propagules such as tubers or shoot parts with buds) or the area on which the plants grow (for example the area under cultivation). The compounds according to the invention can be deployed, for example, prior to sowing (if appropriate also by incorporation into the soil), prior to emergence or after emergence. Specific examples of some representatives of the monocotyledonous and dicotyledonous weed flora which can be controlled by the compounds according to the invention are as follows, though the enumeration is not intended to impose a restriction to particular species.

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

When the compounds according to the invention are applied to the soil surface before germination, either the weed seedlings are prevented completely from emerging or the weeds grow until they have reached the cotyledon stage, but then stop growing and eventually, after three to four weeks have elapsed, die completely.

If the active compounds are applied post-emergence to the green parts of the plants, growth stops after the treatment, and the harmful plants remain at the growth stage at the time of application, or they die completely after a certain time, so that in this manner competition by the weeds, which is harmful to the crop plants, is eliminated very early and in a lasting manner.

Although the compounds according to the invention display an outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia,* or monocotyledonous crops of the genera *Allium, Ananas, Asparagus, Avena, Hordeum, Oryza, Panicum, Saccharum, Secale, Sorghum, Triticale, Triticum, Zea,* in particular *Zea* and *Triticum*, are damaged only to an insignificant extent, or not at all, depending on the structure of the respective compound according to the invention and its application rate. For these reasons, the present compounds are very suitable for the selective control of unwanted plant growth in plant crops such as agriculturally useful plants or ornamentals.

In addition, the compounds according to the invention (depending on their particular structure and the application rate deployed) have outstanding growth-regulating properties in crop plants. They intervene to regulate the plant's metabolism and can thus be used for controlled influence on plant constituents and to facilitate harvesting, for example by triggering desiccation and stunted growth. In addition, they are also suitable for general control and inhibition of unwanted vegetative growth without killing the plants in the process. Inhibiting vegetative growth plays a major role for many monocotyledonous and dicotyledonous crops, since, for example, this can reduce or completely prevent lodging.

By virtue of their herbicidal and plant-growth-regulating properties, the active compounds can also be used for controlling harmful plants in crops of genetically modified plants or plants modified by conventional mutagenesis. In general, transgenic plants are notable for special advantageous properties, for example for resistances to certain pesticides, in particular certain herbicides, resistances to plant diseases or organisms that cause plant diseases, such as certain insects or microorganisms such as fungi, bacteria or viruses. Other particular properties relate, for example, to the harvested material with regard to quantity, quality, storability, composition and specific constituents. For instance, there are known transgenic plants with an elevated starch content or altered starch quality, or those with a different fatty acid composition in the harvested material.

It is preferred, with respect to transgenic crops, to use the compounds according to the invention in economically important transgenic crops of useful plants and ornamentals, for example of cereals such as wheat, barley, rye, oats, millet/sorghum, rice and corn or else crops of sugar beet, cotton, soybean, oilseed rape, potato, tomato, peas and other vegetables. It is preferred to employ the compounds according to the invention as herbicides in crops of useful plants which are resistant, or have been made resistant by recombinant means, to the phytotoxic effects of the herbicides.

Preference is given to the use of the compounds according to the invention or salts thereof in economically important transgenic crops of useful plants and ornamentals, for example of cereals such as wheat, barley, rye, oats, millet/sorghum, rice, cassava and corn, or else crops of sugar beet, cotton, soybean, oilseed rape, potato, tomato, peas and other vegetables. Preferably, the compounds according to the invention can be used as herbicides in crops of useful plants which are resistant, or have been made resistant by recombinant means, to the phytotoxic effects of the herbicides.

Conventional ways of producing novel plants which have modified properties in comparison to plants which have occurred to date consist, for example, in traditional breeding methods and the generation of mutants. Alternatively, novel plants with modified properties can be generated with the aid of recombinant methods (see, for example, EP-A-0221044, EP-A-0131624). For example, there have been many descriptions of

- recombinant modifications of crop plants for the purpose of modifying the starch synthesized in the plants (e.g. WO 92/11376, WO 92/14827, WO 91/19806),
- transgenic crop plants which are resistant to particular herbicides of the glufosinate type (cf., for example, EP-A-0242236, EP-A-242246) or glyphosate type (WO 92/00377) or of the sulfonylurea type (EP-A-0257993, U.S. Pat. No. 5,013,659),
- transgenic crop plants, for example cotton, with the ability to produce *Bacillus thuringiensis* toxins (Bt toxins) which make the plants resistant to particular pests (EP-A-0142924, EP-A-0193259).
- transgenic crop plants with a modified fatty acid composition (WO 91/13972).
- genetically modified crop plants with novel constituents or secondary metabolites, for example novel phytoalexins, which bring about an increased disease resistance (EPA 309862, EPA0464461)
- genetically modified plants with reduced photorespiration which feature higher yields and higher stress tolerance (EPA 0305398).
- transgenic crop plants which produce pharmaceutically or diagnostically important proteins ("molecular pharming")
- transgenic crop plants which feature higher yields or better quality
- transgenic crop plants which are distinguished by a combination, for example, of the abovementioned novel properties ("gene stacking")

A large number of molecular-biological techniques by means of which novel transgenic plants with modified properties can be generated are known in principle; see, for example, I. Potrykus and G. Spangenberg (eds.) Gene Transfer to Plants, Springer Lab Manual (1995), Springer Verlag Berlin, Heidelberg, or Christou, "Trends in Plant Science" 1 (1996) 423-431.

For such recombinant manipulations, nucleic acid molecules which allow mutagenesis or a sequence change by recombination of DNA sequences can be introduced into plasmids. With the aid of standard methods, it is possible, for example, to undertake base exchanges, remove parts of sequences or add natural or synthetic sequences. For the joining of the DNA fragments to one another, adaptors or linkers can be attached to the fragments; see, for example, Sambrook et al., 1989, Molecular Cloning, A Laboratory Manual, 2nd ed. Cold Spring Harbor Laboratory Press, Cold Spring Harbor, N.Y.; or Winnacker "Gene and Klone" [Genes and Clones], VCH Weinheim 2nd edition 1996.

For example, the generation of plant cells with a reduced activity of a gene product can be achieved by expressing at least one corresponding antisense RNA, a sense RNA for achieving a cosuppression effect, or by expressing at least one suitably constructed ribozyme which specifically cleaves transcripts of the abovementioned gene product. To this end, it is possible firstly to use DNA molecules which encompass the entire coding sequence of a gene product inclusive of any flanking sequences which may be present, and also DNA molecules which only encompass portions of the coding sequence, it being necessary for these portions to be long enough to have an antisense effect in the cells. It is also possible to use DNA sequences which have a high degree of homology to the coding sequences of a gene product, but are not completely identical.

When expressing nucleic acid molecules in plants, the protein synthesized can be localized in any desired compartment of the plant cell. However, in order to achieve localization in a particular compartment, it is possible, for example, to join the coding region to DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give whole plants. In principle, the transgenic plants may be plants of any desired plant species, i.e. both monocotyledonous and dicotyledonous plants.

For instance, it is possible to obtain transgenic plants whose properties are altered by overexpression, suppression or inhibition of homologous (=natural) genes or gene sequences, or expression of heterologous (=foreign) genes or gene sequences.

Preferably, the compounds according to the invention can be used in transgenic crops which are resistant to growth regulators, for example dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulfonylureas, the glyphosates, glufosinates or benzoylisoxazoles and analogous active compounds.

On employment of the active compounds according to the invention in transgenic crops, not only do the effects toward harmful plants to be observed in other crops occur, but often also effects which are specific to application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also provides for the use of the compounds according to the invention as herbicides for control of harmful plants in transgenic crop plants.

The compounds according to the invention can be applied in the form of wettable powders, emulsifiable concentrates, sprayable solutions, dusting products or granules in the customary formulations. The invention therefore also provides herbicidal and plant-growth-regulating compositions which comprise the compounds according to the invention.

The compounds according to the invention can be formulated in various ways, according to the biological and/or physicochemical parameters required. Examples of possible formulations include: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for broadcasting and soil application, granules (GR) in the form of microgranules, sprayable granules, coated granules and adsorption granules, water-dispersible granules (WG), water-soluble granules (SG), ULV formulations, microcapsules and waxes.

These individual formulation types are known in principle and are described, for example, in: Winnacker-Küchler, "Chemische Technologie" [Chemical Technology], volume 7, C. Hanser Verlag Munich, 4th ed. 1986; Wade van Valkenburg, "Pesticide Formulations", Marcel Dekker, N.Y., 1973; K. Martens, "Spray Drying" Handbook, 3rd ed. 1979, G. Goodwin Ltd. London.

The necessary formulation assistants, such as inert materials, surfactants, solvents and further additives, are likewise known and are described, for example, in: Watkins, "Handbook of Insecticide Dust Diluents and Carriers", 2nd ed., Darland Books, Caldwell N.J., H.v. Olphen, "Introduction to Clay Colloid Chemistry"; 2nd ed., J. Wiley & Sons, N.Y.; C. Marsden, "Solvents Guide"; 2nd ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schonfeldt, "Grenzflächenaktive Äthylenoxiddadukte" [Interface-active Ethylene Oxide Adducts], Wiss. Verlagsgesell., Stuttgart 1976; Winnacker-Küchler, "Chemische Technologie" [Chemical Technology], volume 7, C. Hanser Verlag Munich, 4th ed. 1986.

Based on these formulations, it is also possible to produce combinations with other pesticidally active substances, such as, for example, insecticides, acaricides, herbicides, fungicides, and also with safeners, fertilizers and/or growth regulators, for example in the form of a finished formulation or as a tank mix. Suitable safeners are, for example, mefenpyr-diethyl, cyprosulfamide, isoxadifen-ethyl, cloquintocet-mexyl and dichlormid.

Wettable powders are preparations which can be dispersed uniformly in water and, in addition to the active ingredient, apart from a diluent or inert substance, also comprise surfactants of the ionic and/or nonionic type (wetting agents, dispersants), for example polyoxyethylated alkylphenols, polyethoxylated fatty alcohols, polyoxyethylated fatty amines, fatty alcohol polyglycol ether sulfates, alkanesulfonates, alkylbenzenesulfonates, sodium lignosulfonate, sodium 2,2' dinaphthylmethane-6,6'-disulfonate, sodium dibutylnaphthalenesulfonate or else sodium oleoylmethyltaurate. To prepare the wettable powders, the herbicidally active compounds are ground finely, for example in customary apparatus such as hammer mills, blower mills and air-jet mills, and simultaneously or subsequently mixed with the formulation auxiliaries.

Emulsifiable concentrates are produced by dissolving the active compound in an organic solvent, for example butanol, cyclohexanone, dimethylformamide, xylene, or else relatively high-boiling aromatics or hydrocarbons or mixtures of the organic solvents, with addition of one or more ionic and/or nonionic surfactants (emulsifiers). Emulsifiers used may, for example, be: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxideethylene oxide condensation products, alkyl polyethers, sorbitan esters, for example sorbitan fatty acid esters, or polyoxyethylene sorbitan esters, for example polyoxyethylene sorbitan fatty acid esters.

Dusts are obtained by grinding the active compound with finely distributed solid substances, for example talc, natural clays, such as kaolin, bentonite and pyrophyllite, or diatomaceous earth.

Suspension concentrates may be water- or oil-based. They can be produced, for example, by wet grinding by means of commercial bead mills with optional addition of surfactants as already listed above, for example, for the other formulation types.

Emulsions, for example oil-in-water emulsions (EW), can be produced, for example, by means of stirrers, colloid mills and/or static mixers using aqueous organic solvents and optionally surfactants as already listed above, for example, for the other formulation types.

Granules can be prepared either by spraying the active compound onto adsorptive granular inert material or by applying active compound concentrates to the surface of carriers, such as sand, kaolinites or granular inert material, by means of adhesives, for example polyvinyl alcohol, sodium polyacrylates or else mineral oils. Suitable active compounds can also be granulated in the manner customary for the production of fertilizer granules—if desired as a mixture with fertilizers.

Water-dispersible granules are prepared generally by the customary processes such as spray-drying, fluidized bed granulation, pan granulation, mixing with high-speed mixers and extrusion without solid inert material.

For the production of pan granules, fluidized bed granules, extruder granules and spray granules, see, for example, processes in "Spray-Drying Handbook" 3rd ed. 1979, G. Goodwin Ltd., London, J. E. Browning, "Agglomeration", Chemical and Engineering 1967, pages 147 ff.; "Perry's Chemical Engineer's Handbook", 5th ed., McGraw-Hill, New York 1973, pp. 8-57.

For further details regarding the formulation of crop protection agents, see, for example, G. C. Klingman, "Weed Control as a Science", John Wiley and Sons, Inc., New York, 1961, pages 81-96 and J. D. Freyer, S. A. Evans, "Weed Control Handbook", 5th ed., Blackwell Scientific Publications, Oxford, 1968, pages 101-103.

The agrochemical preparations contain generally 0.1 to 99% by weight, especially 0.1 to 95% by weight, of compounds according to the invention.

In wettable powders, the active compound concentration is, for example, about 10 to 90% by weight, the remainder to 100% by weight consisting of customary formulation constituents. In emulsifiable concentrates, the active compound concentration may be about 1 to 90% and preferably 5 to 80% by weight. Formulations in the form of dusts comprise 1 to 30% by weight of active compound, preferably usually 5 to 20% by weight of active compound; sprayable solutions contain about 0.05 to 80% and preferably 2 to 50% by weight of active compound. In the case of water-dispersible granules, the active compound content depends partly on whether the active compound is present in liquid or solid form and on which granulation assistants, fillers, etc., are used. In the water-dispersible granules, the content of active compound is, for example, between 1 and 95% by weight, preferably between 10 and 80% by weight.

In addition, the active compound formulations mentioned optionally comprise the respective customary tackifiers, wetting agents, dispersants, emulsifiers, penetrants, preservatives, antifreeze agents and solvents, fillers, carriers and dyes, defoamers, evaporation inhibitors and agents which influence the pH and the viscosity.

Based on these formulations, it is also possible to produce combinations with other pesticidally active substances, such as, for example, insecticides, acaricides, herbicides, fungicides, and also with safeners, fertilizers and/or growth regulators, for example in the form of a finished formulation or as a tank mix.

For application, the formulations in commercial form are, if appropriate, diluted in a customary manner, for example in the case of wettable powders, emulsifiable concentrates, dispersions and water-dispersible granules with water. Preparations in the form of dusts, granules for soil application or granules for sowing and sprayable solutions are usually not diluted further with other inert substances prior to application.

The required application rate of the compounds of the formula (I) varies with the external conditions, including temperature, humidity and the type of herbicide used. It can vary within wide limits, for example between 0.001 and 1.0 kg/ha or more of active substance, but it is preferably between 0.005 and 750 g/ha.

The examples below illustrate the invention.

A. Chemical Examples

Synthesis of 2-methyl-3-methylsulfonyl-4-trifluorometyl-N-(1-propyltetrazol-5-yl)thiobenzamide
(No. 1-9)

196 mg (0.5 mmol) of 2-methyl-3-methylsulfonyl-4-trifluorometyl-N-(1-propyltetrazol-5-yl)benzamide and 404 mg (1 mmol) of Lawesson's reagent in 5 ml of dioxane are heated under reflux for 5 h. After the end of the reaction, 1 ml of water is added, the mixture is concentrated and the residue is purified chromatographically by HPLC, giving 158 mg of 2-methyl-3-methylsulfonyl-4-trifluorometyl-N-(1-propyltetrazol-5-yl)thiobenzamide (yield: 78%).

The examples listed in the tables below were prepared analogously to the abovementioned methods or are obtainable analogously to the abovementioned methods. The compounds listed in the tables below are very particularly preferred.

The abbreviations used mean:
Et=ethyl Me=methyl n-Pr=n-propyl c-Pr=c-propyl

TABLE 1

Compounds of the general formula (I) in which A represents CY and B represents N and W represents hydrogen

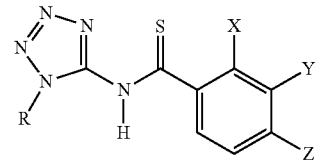

| Ex. No. | R | X | Y | Z | Physical data ($^1$H-NMR, DMSO-d$_6$, 400 MHz) |
|---|---|---|---|---|---|
| 1-1 | Me | Cl | H | SO$_2$Me | |
| 1-2 | Me | SO$_2$Me | H | CF$_3$ | 8.26 (s, 1H), 8.23 (d, 1H), 7.89 (d, 1H), 4.08 (s, 3H), 3.48 (s, 3H) |
| 1-3 | Me | Me | SMe | CF$_3$ | |
| 1-4 | MeOC$_2$H$_4$ | Me | SMe | CF$_3$ | |
| 1-5 | Me | Me | SOMe | CF$_3$ | |
| 1-6 | Et | Me | SOMe | CF$_3$ | |
| 1-7 | Me | Me | SO$_2$Me | CF$_3$ | 8.00 (d, 1H), 7.94 (d, 1H), 4.05 (s, 3H), 3.44 (s, 3H), 2.78 (s, 3H) |
| 1-8 | Et | Me | SO$_2$Me | CF$_3$ | 7.99 (d, 1H), 7.92 (d, 1H), 4.36 (q, 2H), 3.43 (s, 3H), 2.79 (s, 3H), 1.49 (t, 3H) |
| 1-9 | Pr | Me | SO$_2$Me | CF$_3$ | 7.99 (d, 1H), 7.90 (d, 1H), 4.29 (t, 2H), 3.43 (s, 3H), 2.79 (s, 3H), 1.90 (m, 2H), 0.89 (t, 3H) |
| 1-10 | MeOC$_2$H$_4$ | Me | SO$_2$Me | CF$_3$ | |
| 1-11 | Me | Me | SEt | CF$_3$ | |

TABLE 1-continued

Compounds of the general formula (I) in which A represents CY and B represents N and W represents hydrogen

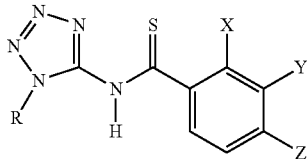

| Ex. No. | R | X | Y | Z | Physical data ($^1$H-NMR, DMSO-$d_6$, 400 MHz) |
|---|---|---|---|---|---|
| 1-12 | Et | Me | SEt | $CF_3$ | |
| 1-13 | Me | Me | SOEt | $CF_3$ | |
| 1-14 | Et | Me | SOEt | $CF_3$ | |
| 1-15 | Me | Me | $SO_2$Et | $CF_3$ | |
| 1-16 | Et | Me | $SO_2$Et | $CF_3$ | |
| 1-17 | Me | Me | $SO_2$Me | Cl | |
| 1-18 | Me | Me | SEt | Cl | |
| 1-19 | Me | Me | SOEt | Cl | |
| 1-20 | Et | Me | SOEt | Cl | |
| 1-21 | Me | Me | $SO_2$Et | Cl | |
| 1-22 | Me | Me | SMe | Br | |
| 1-23 | Me | Me | SEt | Br | |
| 1-24 | Me | Me | 4,5-dihydro-1,2-oxazol-3-yl | $SO_2$Me | |
| 1-25 | Et | Me | 4,5-dihydro-1,2-oxazol-3-yl | $SO_2$Me | |
| 1-26 | Me | Me | pyrazol-1-yl | $SO_2$Me | 8.07 (d, 1H), 7.78 (d, 1H), 7.91 (d, 1H), 7.86 (d, 1H), 6.60 (t, 1H), 4.04 (s, 3H), 3.03 (s, 3H), 1.92 (s, 3H) |
| 1-27 | Et | Me | pyrazol-1-yl | $SO_2$Me | |
| 1-28 | Et | Me | F | $SO_2$Me | 13.0 (brs, 1H), 7.80 (t, 1H), 7.56 (d, 1H), 4.35 (q, 3H), 3.38 (s, 3H), 2.39 (s, 3H), 1.50 (t, 3H) |
| 1-29 | Me | Me | Cl | $SO_2$Me | 12.8 (brs, 1H), 8.01 (d, 1H), 7.70 (d, 1H), 4.05 (s, 3H), 3.43 (s, 3H), 2.49 (s, 3H) |
| 1-30 | Me | Me | OMe | $SO_2$Me | 7.79 (d, 1H), 7.36 (d, 1H), 4.10 (s, 3H), 3.95 (s, 3H), 3.23 (s, 3H), 2.47 (s, 3H) |
| 1-31 | Me | Me | SMe | $SO_2$Me | |
| 1-32 | Me | Me | $SO_2$Me | $SO_2$Me | |
| 1-33 | Et | Me | $SO_2$Me | $SO_2$Me | |
| 1-34 | Me | Me | $SO_2$Et | $SO_2$Me | |
| 1-35 | Et | Me | $SO_2$Et | $SO_2$Me | |
| 1-36 | Me | Et | SMe | $CF_3$ | |
| 1-37 | Me | Et | SOMe | $CF_3$ | |
| 1-38 | Me | Et | $SO_2$Me | $CF_3$ | |
| 1-39 | Me | Et | SMe | Cl | |
| 1-40 | Et | Et | SMe | Cl | |
| 1-41 | Me | Et | SOMe | Cl | |
| 1-42 | Me | Et | SMe | Br | |
| 1-43 | Me | Et | $SO_2$Me | Br | |
| 1-44 | Me | Pr | SMe | $CF_3$ | |
| 1-45 | Me | Pr | SOMe | $CF_3$ | |
| 1-46 | Me | c-Pr | SMe | $CF_3$ | |
| 1-47 | Me | OMe | SMe | $CHF_2$ | |
| 1-48 | Et | OMe | SMe | $CHF_2$ | |
| 1-49 | Me | OMe | SOMe | $CHF_2$ | |
| 1-50 | Et | OMe | SOMe | $CHF_2$ | |
| 1-51 | Me | OMe | $SO_2$Me | $CHF_2$ | |
| 1-52 | Et | OMe | $SO_2$Me | $CHF_2$ | |
| 1-53 | Me | OMe | SEt | $CHF_2$ | |
| 1-54 | Me | OMe | SMe | $CF_3$ | 12.95 (brs, 1H), 7.73 (d, 1H), 7.66 (d, 1H), 4.04 (s, 3H), 3.98 (s, 3H), 2.48 (s, 3H) |
| 1-55 | Et | OMe | SMe | $CF_3$ | |
| 1-56 | Me | OMe | SOMe | $CF_3$ | |
| 1-57 | Et | OMe | SOMe | $CF_3$ | |
| 1-58 | Me | OMe | $SO_2$Me | $CF_3$ | |
| 1-59 | Et | OMe | $SO_2$Me | $CF_3$ | |
| 1-60 | Me | OMe | SEt | $CF_3$ | |
| 1-61 | Me | Cl | SMe | H | |
| 1-62 | Me | Cl | SMe | Me | |

TABLE 1-continued

Compounds of the general formula (I) in which A represents CY and B represents N and W represents hydrogen

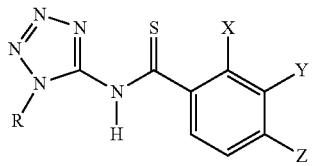

| Ex. No. | R | X | Y | Z | Physical data (¹H-NMR, DMSO-$d_6$, 400 MHz) |
|---|---|---|---|---|---|
| 1-63 | Me | Cl | SO$_2$Me | Me | 7.65 (d, 1H), 7.34 (d, 1H), 4.10 (s, 3H), 3.32 (s, 3H), 2.79 (s, 3H) |
| 1-64 | Me | Cl | SO$_2$Et | Me | |
| 1-65 | Me | Cl | SO$_2$Me | CF$_3$ | |
| 1-66 | Me | Cl | OC$_2$H$_4$OMe | Cl | |
| 1-67 | Me | Cl | SMe | Cl | |
| 1-68 | Et | Cl | SMe | Cl | |
| 1-69 | Me | Cl | SOMe | Cl | |
| 1-70 | Et | Cl | SOMe | Cl | |
| 1-71 | Me | Cl | SO$_2$Me | Cl | |
| 1-72 | Et | Cl | SO$_2$Me | Cl | |
| 1-73 | Me | Cl | SO$_2$Et | Cl | |
| 1-74 | Me | Cl | CH$_2$OMe | SO$_2$Me | 8.05 (d, 1H), 7.65 (d, 1H), 5.07 (s, 2H), 4.09 (s, 3H), 3.51 (s, 3H), 3.24 (s, 3H) |
| 1-75 | Me | Cl | CH$_2$OCH$_2$CF$_3$ | SO$_2$Me | 13.2 (brs, 1H), 8.09 (d, 1H), 7.91 (d, 1H), 5.26 (s, 2H), 4.31 (q, 2H), 4.05 (s, 3H), 3.37 (s, 3H) |
| 1-76 | Et | Cl | CH$_2$OCH$_2$CF$_3$ | SO$_2$Me | |
| 1-77 | Me | Cl | CH$_2$OC$_2$H$_4$OMe | SO$_2$Me | |
| 1-78 | Me | Cl | 4,5-dihydro-1,2-oxazol-3-yl | SO$_2$Me | |
| 1-79 | Me | Cl | 4,5-dihydro-1,2-oxazol-3-yl | SO$_2$Et | |
| 1-80 | Me | Cl | 5-methoxymethy-4,5-dihydro-1,2-oxazol-3-yl | SO$_2$Et | |
| 1-81 | Me | Cl | OMe | SO$_2$Me | 7.93 (d, 1H), 7.48 (d, 1H), 4.11 (s, 3H), 4.10 (s, 3H), 3.26 (s, 3H) |
| 1-82 | Me | Cl | OMe | SO$_2$Et | |
| 1-83 | Me | Cl | OEt | SO$_2$Me | 7.94 (d, 1H), 7.46 (d, 1H), 4.34 (q, 2H), 4.10 (s, 3H), 3.28 (s, 3H), 1.53 (t, 3H) |
| 1-84 | Me | Cl | OEt | SO$_2$Et | |
| 1-85 | Me | Cl | OPr | SO$_2$Me | |
| 1-86 | Me | Cl | OPr | SO$_2$Et | |
| 1-87 | Me | Cl | Oi-Bu | SO$_2$Me | |
| 1-88 | Me | Cl | OCH$_2$c-Pr | SO$_2$Me | 7.93 (d, 1H), 7.46 (d, 1H), 4.11 (d, 2H), 4.09 (s, 3H), 3.32 (s, 3H), 1.40-1.55 (m, 1H), 0.64-0.71 (m, 2H), 0.43-0.50 (m, 2H) |
| 1-89 | Me | Cl | OCH$_2$c-Pr | SO$_2$Et | |
| 1-90 | Me | Cl | OC$_2$H$_4$OMe | SO$_2$Me | |
| 1-91 | Me | Cl | OC$_3$H$_6$OMe | SO$_2$Me | 7.92 (d, 1H), 7.47 (d, 1H), 4.35 (t, 2H) 4.10 (s, 3H), 3.62 (t, 2H), 3.37 (s, 3H), 3.26 (s, 3H), 2.18 (quin, 2H) |
| 1-92 | Me | Cl | SMe | SO$_2$Me | |

TABLE 2

Compounds of the general formula (I) in which A represents CY and B represents CH and W represents hydrogen

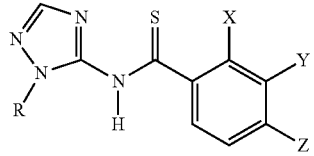

| Ex. No. | R | X | Y | Z | Physical data (¹H-NMR, DMSO-$d_6$, 400 MHz) |
|---|---|---|---|---|---|
| 2-1 | Me | Me | $SO_2Me$ | $CF_3$ | |
| 2-2 | Me | Me | 4,5-dihydro-1,2-oxazol-3-yl | $SO_2Me$ | |
| 2-3 | Me | Me | pyrazol-1-yl | $SO_2Me$ | |
| 2-4 | Me | Me | $SO_2Me$ | $SO_2Me$ | 8.20 (brs, 1H), 8.19 (d, 1H), 7.88 (brs, 1H), 3.79 (s, 3H), 3.58 (s, 3H), 3.56 (s, 3H), 2.71 (s, 3H) |
| 2-5 | Me | Cl | $SO_2Me$ | Cl | |
| 2-6 | Me | Cl | 4,5-dihydro-1,2-oxazol-3-yl | $SO_2Me$ | |
| 2-7 | Me | Cl | 4,5-dihydro-1,2-oxazol-3-yl | $SO_2Et$ | |
| 2-8 | Me | Cl | $OC_2H_4OMe$ | $SO_2Me$ | |

TABLE 3

Compounds of the general formula (I) in which A represents CY and B represents N

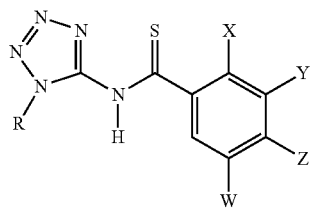
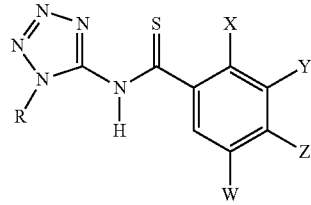

| Ex. No. | R | X | Y | Z | W | Physical data (¹H-NMR, DMSO-$d_6$, 400 MHz) |
|---|---|---|---|---|---|---|
| 3-1 | Me | Cl | H | SMe | Me | 12.85 (brs, 1H), 7.47 (s, 1H), 7.27 (s, 1H), 4.02 (s, 3H), 2.56 (s, 3H), 2.26 (s, 3H) |
| 3-2 | Me | Cl | SMe | H | Me | |
| 3-3 | Me | Cl | $SO_2Me$ | H | Me | |
| 3-4 | Et | Cl | $SO_2Me$ | H | Me | |
| 3-5 | Me | Cl | Me | SMe | Me | |
| 3-6 | Et | Cl | Me | $SO_2Me$ | Me | |
| 3-7 | Me | Br | $SO_2Me$ | H | Me | |
| 3-8 | Me | Cl | OMe | SMe | OMe | |

TABLE 4

Compounds of the general formula (I) in which A and B each represent N and W represents hydrogen

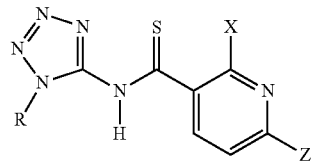

| Ex. No. | R | X | Z | Physical data (¹H-NMR, DMSO-$d_6$, 400 MHz) |
|---|---|---|---|---|
| 4-1 | Me | Me | $CF_3$ | 13.1 (brs, 1H), 8.17 (d, 1H), 7.88 (d, 1H), 4.06 (s, 3H), 2.68 (s, 3H) |
| 4-2 | Me | $CH_2OMe$ | $CF_3$ | 13.1 (brs, 1H), 8.25 (d, 1H), 8.02 (d, 1H), 4.79 (s, 2H), 4.05 (s, 3H), 3.17 (s, 3H) |
| 4-3 | Et | $CH_2OMe$ | $CF_3$ | |
| 4-4 | Me | $CH_2OC_2H_4OMe$ | $CF_3$ | |

TABLE 4-continued

Compounds of the general formula (I) in which A and B each represent N and W represents hydrogen

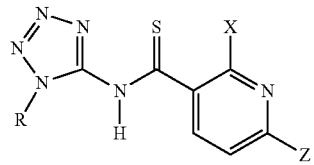

| Ex. No. | R  | X          | Z   | Physical data (¹H-NMR, DMSO-$d_6$, 400 MHz) |
|---------|----|------------|-----|---------------------------------------------|
| 4-5     | Et | $CH_2OC_2H_4OMe$ | $CF_3$ |                                          |
| 4-6     | Me | $CH_2OCH_2$c-Pr | $CF_3$ |                                          |
| 4-7     | Me | Cl         | $CF_3$ | 8.38 (d, 1H), 8.09 (d, 1H), 4.03 (s, 3H)  |
| 4-8     | Me | Br         | $CF_3$ |                                          |
| 4-9     | Me | $SO_2Me$   | $CF_3$ |                                          |
| 4-10    | Me | SMe        | SMe  | 7.73 (d, 1H), 7.12 (d, 1H), 4.02 (s, 3H), 2.60 (s, 3H), 2.54 (s, 3H) |

B. Formulation Examples a) A dusting product is obtained by mixing 10 parts by weight of a compound of the formula (I) and/or salts thereof and 90 parts by weight of talc as an inert substance and comminuting the mixture in a hammer mill.

b) A readily water-dispersible, wettable powder is obtained by mixing 25 parts by weight of a compound of the formula (I) and/or salts thereof, 64 parts by weight of kaolin-containing quartz as an inert substance, 10 parts by weight of potassium lignosulfonate and 1 part by weight of sodium oleoylmethyltaurate as a wetting agent and dispersant, and grinding the mixture in a pinned-disk mill.

c) A readily water-dispersible dispersion concentrate is obtained by mixing 20 parts by weight of a compound of the formula (I) and/or salts thereof with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277 C), and grinding the mixture in a ball mill to a fineness of below 5 microns.

d) An emulsifiable concentrate is obtained from 15 parts by weight of a compound of the formula (I) and/or salts thereof, 75 parts by weight of cyclohexanone as a solvent and 10 parts by weight of ethoxylated nonylphenol as an emulsifier.

e) Water-dispersible granules are obtained by mixing
  75 parts by weight of a compound of the formula (I) and/or salts thereof,
  10 parts by weight of calcium lignosulfonate,
  5 parts by weight of sodium laurylsulfate,
  3 parts by weight of polyvinyl alcohol and
  7 parts by weight of kaolin,
  grinding the mixture in a pinned-disk mill and granulating the powder in a fluidized bed by spraying on water as a granulating liquid.

f) Water-dispersible granules are also obtained by homogenizing and precomminuting
  25 parts by weight of a compound of the formula (I) and/or salts thereof,
  5 parts by weight of sodium 2,2'-dinaphthylmethane-6,6'-disulfonate,
  2 parts by weight of sodium oleoylmethyltaurate,
  1 part by weight of polyvinyl alcohol,
  17 parts by weight of calcium carbonate and
  50 parts by weight of water
  in a colloid mill, then grinding the mixture in a bead mill and atomizing and drying the resulting suspension in a spray tower by means of a one-phase nozzle.

C. Biological Examples

1. Pre-Emergence Herbicidal Action Against Harmful Plants

Seeds of monocotyledonous and dicotyledonous weed plants and crop plants are placed in wood-fiber pots in sandy loam and covered with soil. The compounds according to the invention, formulated in the form of wettable powders (WP) or as emulsion concentrates (EC), are then applied as aqueous suspension or emulsion at a water application rate of 600 to 800 I/ha (converted) with the addition of 0.2% of wetting agent to the surface of the covering soil. After the treatment, the pots are placed in a greenhouse and kept under good growth conditions for the test plants. The damage to the test plants is assessed visually after a test period of 3 weeks by comparison with untreated controls (herbicidal activity in percent (%): 100% action=the plants have died, 0% action=like control plants). Here, for example, the compounds Nos 1-8, 1-26 and 4-7, at an application rate of 80 g/ha, show an activity of at least 80% against *Alopecurus myosuroides, Avena fatua, Cyperus serotinus, Echinochloa crus galli, Lolium multiflorum, Setaria viridis, Abutilon theophrasti, Amaranthus retroflexus, Matricaria inodora, Pharbitis purpureum, Stellaria media, Viola tricolor* and *Veronica persica*.

2. Post-Emergence Herbicidal Action Against Harmful Plants

Seeds of monocotyledonous and dicotyledonous weed and crop plants are placed in sandy loam in wood-fiber pots, covered with soil and cultivated in a greenhouse under good growth conditions. 2 to 3 weeks after sowing, the test plants are treated at the one-leaf stage. The compounds according to the invention, formulated in the form of wettable powders (WP) or as emulsion concentrates (EC), are then sprayed as aqueous suspension or emulsion at a water application rate of 600 to 800 I/ha (converted) with the addition of 0.2% of wetting agent onto the green parts of the plants. After the test plants have been left to stand in the greenhouse under optimal growth conditions for about 3 weeks, the action of the preparations is assessed visually in comparison to untreated controls (herbicidal action in percent (%): 100% action=the plants have died, 0% action=like control plants). Here, for example, the compounds Nos 1-8 and 1-83, at an application rate of 80 g/ha, show an activity of at least 80% against *Alopecurus myosuroides, Avena fatua, Cyperus serotinus, Echinochloa crus galli, Lolium multiflorum, Setaria viridis, Abutilon theophrasti, Amaranthus retroflexus, Matricaria inodora, Pharbitis purpureum, Polygonum convolvulus, Stellaria media, Viola tricolor* and *Veronica persica*.

3. Comparative Tests

To demonstrate the superiority of the compounds according to the invention, numerous compounds according to the invention were compared in an exemplary manner to the structurally closest compounds, known from WO 2012/028579 A1, at various application rates and with different harmful plants and crop plants. These comparative experiments were carried out under the conditions mentioned above by the pre-emergence method and the post-emergence method. In the tables below, the top line in each case states the compound according to the invention, and the bottom line states the compound from WO 2012/028579 A1.

The abbreviations used here mean:

| Harmful plants | | | |
|---|---|---|---|
| ABUTH | *Abutilon theophrasti* | ALOMY | *Alopecurus myosuroides* |
| AMARE | *Amaranthus retroflexus* | AVEFA | *Avena fatua* |
| CYPES | *Cyperus serotinus* | ECHCG | *Echinochloa crus galli* |
| LOLMU | *Lolium multiflorum* | PHBPU | *Pharbitis purpureum* |
| POLCO | *Polygonum convolvulus* | SETVI | *Setaria viridis* |
| Crop plants | | | |
| BRSNW | *Brassica napus* (oilseed rape) | ORYSA | *Oryza sativa* (rice) |
| TRZAS | *Triticum aestivum* (wheat) | ZEAMX | *Zea mays* (corn) |

TABLE A

| | Pre-emergence action | | | |
|---|---|---|---|---|
| Compound | Dosage [g/ha] | Damage to crop plants BRSNW | Herbicidal efficacy against ABUTH | PHBPU |
| 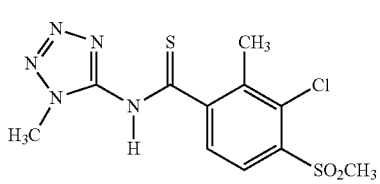 No. 1-29 | 20 | 0% | 90% | 20% |
| 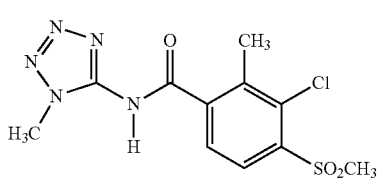 No. 4-173 | 20 | 20% | 70% | 0% |

TABLE B
| | | Pre-emergence action | | |
|---|---|---|---|---|
| Compound | Dosage [g/ha] | Damage to crop plants ORYSA | Herbicidal efficacy against CYPES | ECHCG |
| 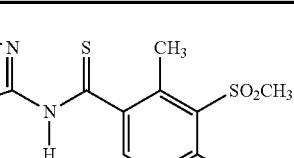 No. 1-9 | 20 | 0% | 100% | 20% |
| 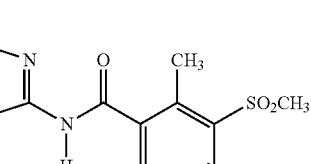 No. 7-032 | 20 | 50% | 0% | 0% |
TABLE C
| | | Pre-emergence action | | |
|---|---|---|---|---|
| Compound | Dosage [g/ha] | Damage to crop plants ZEAMX | Herbicidal efficacy against AVEFA | POLCO |
| No. 1-75 | 320 | 0% | 90% | 90% |
| No. 4-260 | 320 | 20% | 70% | 50% |
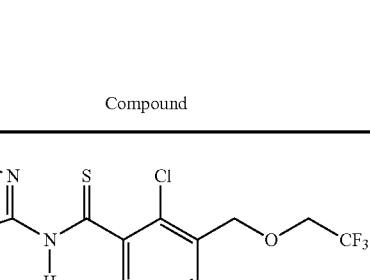

TABLE D

| | | Pre-emergence action | | |
|---|---|---|---|---|
| Compound | Dosage [g/ha] | Damage to crop plants TRZAS | Herbicidal efficacy against | |
| | | | PHBPU | POLCO |
| No. 4-1 | 320 | 0% | 80% | 80% |
| No. 8-19 | 320 | 20% | 60% | 60% |

TABLE E

| | | Pre-emergence action | | |
|---|---|---|---|---|
| Compound | Dosage [g/ha] | Damage to crop plants BRSNW | Herbicidal efficacy against | |
| | | | ABUTH | AMARE |
| No. 2-4 | 320 | 0% | 80% | 90% |
| No. 1-188 | 320 | 20% | 0% | 40% |

TABLE F

Pre-emergence action

| Compound | Dosage [g/ha] | Damage to crop plants | | Herbicidal efficacy against | |
|---|---|---|---|---|---|
| | | BRSNW | ORYSA | ECHCG | POLCO |
| No. 1-7 | 20 | 0% | 20% | 100% | 60% |
| No. 4-137 | 20 | 30% | 50% | 20% | 0% |

TABLE G

Post-emergence action

| Compound | Dosage [g/ha] | Damage to crop plants | | Herbicidal efficacy against | |
|---|---|---|---|---|---|
| | | ORYSA | TRZAS | PHBPU | POLCO |
| No. 1-83 | 5 | 10% | 0% | 80% | 60% |
| No. 4-278 | 5 | 40% | 30% | 20% | 40% |

TABLE H

Post-emergence action

| Compound | Dosage [g/ha] | Herbicidal efficacy against | | |
|---|---|---|---|---|
| | | ECHCG | SETVI | AMARE |
| No. 1-29 (1-methyltetrazol-5-yl thioamide, 2-methyl-3-chloro-4-methylsulfonyl benzene) | 5 | 70% | 40% | 40% |
| No. 4-173 (1-methyltetrazol-5-yl amide, 2-methyl-3-chloro-4-methylsulfonyl benzene) | 5 | 10% | 0% | 20% |

TABLE I

Post-emergence action

| Compound | Dosage [g/ha] | Damage to crop plants ZEAMX | Herbicidal efficacy against | |
|---|---|---|---|---|
| | | | ALOMY | LOLMU |
| No. 1-9 (1-propyltetrazol-5-yl thioamide, 2-methyl-3-methylsulfonyl-4-trifluoromethyl benzene) | 80 | 0% | 80% | 20% |
| No. 7-032 (1-propyltetrazol-5-yl amide, 2-methyl-3-methylsulfonyl-4-trifluoromethyl benzene) | 80 | 20% | 30% | 0% |

TABLE J
| | | Post-emergence action | |
|---|---|---|---|
| Compound | Dosage [g/ha] | Damage to crop plants TRZAS | Herbicidal efficacy against POLCO |
| 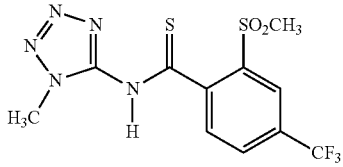<br>No. 1-2 | 80 | 20% | 90% |
| 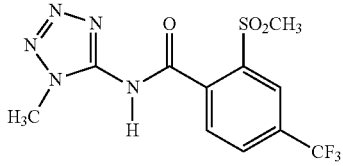<br>No. 4-25 | 80 | 60% | 70% |
TABLE K
| | | Post-emergence action | | |
|---|---|---|---|---|
| | | Damage to crop plants | Herbicidal efficacy against | |
| Compound | Dosage [g/ha] | ZEAMX | AVEFA | LOLMU |
| 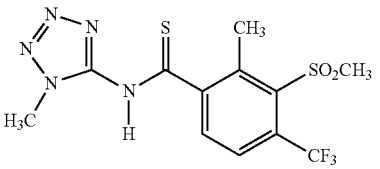<br>No. 1-7 | 80 | 50% | 90% | 90% |
| 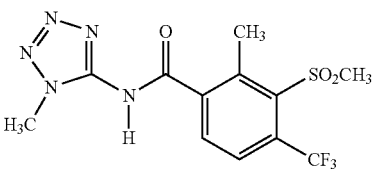<br>No. 4-137 | 80 | 70% | 70% | 70% |

The results of these exploratory comparative experiments show that the compounds according to the invention having a thioamide structure have higher herbicidal activity and cause less damage to crop plants than the structurally closest compounds, known from WO 2012/028579 A1, having an amide structure.

The invention claimed is:

1. An N-(tetrazol-5-yl)- or N-(triazol-5-yl)arylcarboxylic acid thioamide of formula (I) and/or a salt thereof

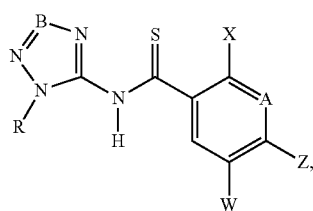

in which
A represents CY,
B represents N,
X represents Cl, $SO_2CH_3$, or methyl,
Y represents hydrogen, $SO_2CH_3$, Cl, $CH_2OCH_2CF_3$, or ethoxy,
Z represents $SO_2CH_3$ or $CF_3$,
W represents hydrogen, and
R represents methyl or propyl.

2. The N-(tetrazol-5-yl)- or N-(triazol-5-yl)arylcarboxylic acid thioamide of formula (I) and/or a salt thereof as claimed in claim 1, in which
A represents CY,
B represents N,
X represents methyl,
Y represents Cl,
Z represents $SO_2CH_3$,
W represents hydrogen, and
R represents methyl.

3. The N-(tetrazol-5-yl)- or N-(triazol-5-yl)arylcarboxylic acid thioamide of formula (I) and/or a salt thereof as claimed in claim 1, in which
A represents CY,
B represents N,
X represents methyl,
Y represents $SO_2CH_3$,
Z represents $CF_3$,
W represents hydrogen, and
R represents propyl.

4. The N-(tetrazol-5-yl)- or N-(triazol-5-yl)arylcarboxylic acid thioamide of formula (I) and/or a salt thereof as claimed in claim 1, in which
A represents CY,
B represents N,
X represents Cl,
Y represents $CH_2OCH_2CF_3$,
Z represents $SO_2CH_3$,
W represents hydrogen, and
R represents methyl.

5. The N-(tetrazol-5-yl)- or N-(triazol-5-yl)arylcarboxylic acid thioamide of formula (I) and/or a salt thereof as claimed in claim 1, in which
A represents CY,
B represents N,
X represents methyl,
Y represents $SO_2CH_3$,
Z represents $CF_3$,
W represents hydrogen, and
R represents methyl.

6. The N-(tetrazol-5-yl)- or N-(triazol-5-yl)arylcarboxylic acid thioamide of formula (I) and/or a salt thereof as claimed in claim 1, in which
A represents CY,
B represents N,
X represents Cl,
Y represents ethoxy,
Z represents $SO_2CH_3$,
W represents hydrogen, and
R represents methyl.

7. The N-(tetrazol-5-yl)- or N-(triazol-5-yl)arylcarboxylic acid thioamide of formula (I) and/or a salt thereof as claimed in claim 1, in which
A represents CY,
B represents N,
X represents $SO_2CH_3$,
Y represents H,
Z represents $CF_3$,
W represents hydrogen, and
R represents methyl.

8. A herbicidal composition which comprises a herbicidally effective amount of at least one compound of formula (I) and/or salt as claimed in claim 1 in a mixture with one or more formulation auxiliaries.

9. A method for controlling one or more unwanted plants, comprising applying an effective amount of at least one compound of formula (I) and/or salt as claimed in claim 1 to a plant and/or to a site of unwanted vegetation.

10. A method for controlling one or more unwanted plants, comprising applying an effective amount of the composition according to claim 8 to a plant and/or to a site of unwanted vegetation.

11. The method as claimed in claim 9, comprising controlling one or more unwanted plants in one or more crops of one or more useful plants.

12. The method as claimed in claim 11, wherein the useful plants are transgenic useful plants.

* * * * *